US010105423B2

(12) United States Patent
Ruddy et al.

(10) Patent No.: US 10,105,423 B2
(45) Date of Patent: *Oct. 23, 2018

(54) C1-INH COMPOSITIONS AND METHODS FOR THE PREVENTION AND TREATMENT OF DISORDERS ASSOCIATED WITH C1 ESTERASE INHIBITOR DEFICIENCY

(71) Applicant: Shire ViroPharma Incorporated, Lexington, MA (US)

(72) Inventors: Stephen Ruddy, Exton, PA (US); Mark Cornell Manning, Johnstown, CO (US); Ryan Erik Holcomb, Fort Collins, CO (US)

(73) Assignee: Shire ViroPharma Incorporated, Lexington, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/837,693

(22) Filed: Dec. 11, 2017

(65) Prior Publication Data

US 2018/0085441 A1 Mar. 29, 2018

Related U.S. Application Data

(63) Continuation of application No. 15/411,744, filed on Jan. 20, 2017, which is a continuation of application No. 14/855,168, filed on Sep. 15, 2015, now Pat. No. 9,616,111, which is a continuation of application No. PCT/US2014/030309, filed on Mar. 17, 2014.

(60) Provisional application No. 61/791,399, filed on Mar. 15, 2013.

(51) Int. Cl.
| | |
|---|---|
| *A61K 38/00* | (2006.01) |
| *A61P 7/00* | (2006.01) |
| *A61K 38/55* | (2006.01) |
| *C07K 14/81* | (2006.01) |
| *A61K 38/57* | (2006.01) |
| *A61K 9/00* | (2006.01) |
| *A61K 47/02* | (2006.01) |
| *A61K 47/12* | (2006.01) |
| *A61K 47/18* | (2017.01) |
| *A61K 47/22* | (2006.01) |
| *A61K 38/17* | (2006.01) |
| *A61K 9/08* | (2006.01) |
| *A61P 31/00* | (2006.01) |

(52) U.S. Cl.
CPC ............ *A61K 38/57* (2013.01); *A61K 9/0019* (2013.01); *A61K 9/08* (2013.01); *A61K 38/00* (2013.01); *A61K 38/1709* (2013.01); *A61K 47/02* (2013.01); *A61K 47/12* (2013.01); *A61K 47/18* (2013.01); *A61K 47/183* (2013.01); *A61K 47/22* (2013.01); *A61P 31/00* (2018.01)

(58) Field of Classification Search
None
See application file for complete search history.

(56) References Cited

U.S. PATENT DOCUMENTS

| | | | |
|---|---|---|---|
| 6,090,777 A | 7/2000 | Hack et al. | |
| 6,875,432 B2 | 4/2005 | Liu et al. | |
| 7,067,713 B2 | 6/2006 | Nuijens et al. | |
| 7,544,853 B2 | 6/2009 | Nuijens | |
| 7,837,992 B2 | 11/2010 | Gurewich et al. | |
| 7,897,561 B2 | 3/2011 | Kotwal et al. | |
| 8,071,532 B2 | 12/2011 | Mannesse et al. | |
| RE43,691 E | 9/2012 | Nuijens | |
| 8,283,319 B2 | 10/2012 | Schulte et al. | |
| 8,415,288 B2 | 4/2013 | Mannesse et al. | |
| 8,501,705 B2 | 8/2013 | Christadoss et al. | |
| 8,652,477 B2 | 2/2014 | Schwaeble et al. | |
| 9,616,111 B2 * | 4/2017 | Ruddy .................. A61K 38/57 |
| 2001/0019839 A1 | 9/2001 | Schoenhofer et al. | |
| 2002/0168352 A1 | 11/2002 | Winkler et al. | |
| 2005/0288218 A1 | 12/2005 | Davis et al. | |
| 2006/0142187 A1 | 6/2006 | Davis et al. | |
| 2006/0233776 A1 | 10/2006 | Heimburger et al. | |
| 2007/0093443 A1 | 4/2007 | Madison et al. | |
| 2007/0192882 A1 | 8/2007 | Dewald | |
| 2010/0143325 A1 | 6/2010 | Gurewich | |
| 2012/0171206 A1 | 7/2012 | Tomlinson et al. | |
| 2012/0244139 A1 | 9/2012 | Madison et al. | |
| 2013/0244941 A1 | 9/2013 | Mannesse et al. | |
| 2014/0234293 A1 | 8/2014 | Basta et al. | |
| 2014/0242062 A1 | 8/2014 | Madison et al. | |
| 2014/0309175 A1 | 10/2014 | Zhao et al. | |
| 2014/0315826 A1 | 10/2014 | Zhao et al. | |
| 2014/0371425 A1 | 12/2014 | Kleinschnitz et al. | |

(Continued)

FOREIGN PATENT DOCUMENTS

| | | |
|---|---|---|
| EP | 2968434 | 6/2017 |
| WO | WO-1992/06203 A1 | 4/1992 |
| WO | WO-1992/22320 A1 | 12/1992 |

(Continued)

OTHER PUBLICATIONS

Jiang et al. "Subcutaneous infusion of human C1 inhibitor in swine" Clinical Immunology 136:323-328. (Year: 2010).*

(Continued)

*Primary Examiner* — Christina Bradley
*Assistant Examiner* — Zachary J Miknis
(74) *Attorney, Agent, or Firm* — Proskauer Rose LLP; Fangli Chen; Julio J. Mendez (57) ABSTRACT

Compositions and methods for the treatment and/or prevention of disorders associated with C1 esterase inhibitor deficiency are disclosed.

29 Claims, 2 Drawing Sheets

Specification includes a Sequence Listing.

(56) References Cited

U.S. PATENT DOCUMENTS

2015/0023977 A1     1/2015    Fraunhofer et al.

FOREIGN PATENT DOCUMENTS

| | | |
|---|---|---|
| WO | WO-1995/06479 A1 | 3/1995 |
| WO | WO-1997/22347 A1 | 6/1997 |
| WO | WO-2001/46219 | 6/2001 |
| WO | WO-2001/57079 | 8/2001 |
| WO | WO-2004/034971 A2 | 4/2004 |
| WO | WO-2004/110356 A2 | 12/2004 |
| WO | WO-2007/047995 A2 | 4/2007 |
| WO | WO-2007/073186 A2 | 6/2007 |
| WO | WO-2009/073569 | 6/2009 |
| WO | WO-2011/003098 A1 | 1/2011 |
| WO | WO-2011/107591 A1 | 9/2011 |
| WO | WO-2011/116291 A1 | 9/2011 |
| WO | WO-2013/013017 A2 | 1/2013 |
| WO | WO-2013/138694 A1 | 9/2013 |
| WO | WO-2013/138730 A1 | 9/2013 |
| WO | WO-2013/138731 A1 | 9/2013 |
| WO | WO-2014/160499 A2 | 10/2014 |

OTHER PUBLICATIONS

Anonymous "Subcutaneous" The Pharmaceutics and Compounding Laboratory. http://pharmlabs.unc.edu/labs/parenterals/subcutaneous.htm. (Year: 2010).*

D'Agnillo F "Summary Basis for Regulatory Action—CINRYZE" FDA. (Year: 2008).*

Anonymous "Cinryze" European Medicines Agency. CHMP assessment report for paediatric use studies submitted according to Article 46 of the Regulation (EC) No. 1901/2006. (Year: 2013).*

Aberer, W., Hereditary angioedema treatment options: The availability of new therapies, Annals of Medicine, 44:523-529 (2012).

Agostoni, A. et al., Hereditary and acquired angioedema: Problems and progress: Proceedings of the third C1 esterase inhibitors deficiency workshop and beyond, Journal of Allergy and Clinical Immunology, 114(3): S51-S131 (2004).

Anonymous. Wikipedia extract: https://en.wikipedia.org/wiki/C1-inhibitor.

Anonymous, Subcutaneous, http://pharmlabs.unc.edu/labs/parenterals/subcutaneous.htm. Published Jun. 14, 2010.

Anonymous. http://www.cslbehring.com/s1/cs/enco/1255923338532/news/1255928832614/prdetail.htm?tabSelections=1255923338570&currentPage=2 ; May 3, 2012.

Anonymous, Phases of Clinical Trials, http://www.virginia.edu/vpr/irb/HSR_docs/CLINICAL_ TRIALS_Phases.pdf. Published Jun. 12, 2012.

Anonymous. News Release, Halozyme Therapeutics (2012). http://www.halozyme.com/investors/news-releases/news-release-details/2012/ViroPharma-and-halozyme-Therapeutics-Announce-Initiation-of-Phase-2b-Dose-Ranging-Combination-Study-for-Subcutaneous-Administration-of-Cinryze-C1-esterase-inhibitor-human-with-hyaluronidase-rhuPH20/default.aspx.

Anonymous. "ViroPharma and Holozyme Therapeutics Announce Initiation of Phase 2b Dose Ranging Combination Study for Subcutaneous Administration of Cinryze ® (C1 esterase inhibitor [human]) with Hyaluronidase (rHuPH20)" Press release, published Dec. 19, 2012.

Anonymous. CINRYZE™ prescribing information, Nov. 2012.

Anonymous. Observations under Section 21 in relation to the patentability of GB1519921.9 of Shire Viropharma Incorporated. Notice from the Observations mailed on Dec. 19, 2016 by the Great Britain Intellectual Property Office.

Anonymous, Third Party Observations in relation to EP 14762343.3, acknowledged by European Patent Office dated Jan. 19, 2017.

Anonymous, Press Release by BMI Research on Mar. 5, 2012, "Subcutaneous Cinryze with rHuPH20 produced positive effects in prevention of HAO," in connection with poster titled "Safety, Pharmacokinetics (PK), and Pharmacodynamics (PD) of Subcutaneous (SC) Cinryze® (C1 Esterase Inhibitor [Human]) with Recombinant Human Hyaluronidase (rHuPH20) in Subjects with Hereditary Angioedema (HAE)."

Anonymous, CSL R&D Briefing, Dec. 5, 2012.

Anonymous, ViroPharma Press release, ViroPharma Provides Update on Phase 2 Clinical Evaluation of Subcutaneous Cinryze® (C1 esterase inhibitor [human]) with Recombinant Human Hyaluronidase (rHuPH20), Aug. 1, 2012.

Anonymous, "Subcutaneous" http://pharmlabs.unc.edu/labs/parenterals/subcutaneous.htm. Published Jun. 14, 2010.

Anonymous, "Plasma Derived Proteins and Enzymes" Bio Files 2006, 1.5, 2. Sigma Aldrich. Published 2006.

Anonymous, "C1 Esterase Inhibitor from human plasma" Sigma Aldrich E0518. Published 2006.

Banerji, A., Current treatment of hereditary angioedema: An update on clinical studies, Allergy and Asthma Proceedings, 31(5):398-406 (2010) (abstract only).

Berinert® approval letter, FDA, Oct. 9, 2009, available at https://www.fda.gov/BiologicsBloodVaccines/BloodBloodProducts/ApprovedProducts/LicensedProductsBLAs/FractionatedPlasmaProducts/ucm186265.htm (downloaded on May 25, 2017).

Berinert® Prescribing Information, CSL Behring, Jul. 2012.

Berinert UK summary-product-characteristics Sep. 2015, available at http://www.medicines.org.uk/emc/print- document?documentId=21650 (downloaded on May 22, 2017).

Bernstein, J.A., Hereditary angioedema: a current state-of-the-art review, VIII: current status of emerging therapies, Annals of Allergy, Asthma & Immunology, 100:S41-S46 (2008).

Bock, S.C. et al., Human C1 Inhibitor: Primary Structure, cDNA Cloning, and Chromosomal Localization, 25 BIOCHEM. 4292-301 (1986). ("Bock").

Bork, K. et al., A Review of Hereditary Angioedema and Recombinant Human C1-Inhibitor Treatment, Hereditary Angioedema, European Respiratory Disease, 32-35 (2011).

Bork, K. et al., Treatment of acute edema attacks in hereditary angioedema with a bradykinin receptor-2 antagonist (Icatibant), J Allergy Clin Immunol, 119(6):1497-1503 (2007).

Bork, K., German Guideline for Hereditary Angioedema a due to C1-INH Deficiency, German Association of Scientific Medical Societies, 1-24 (2011).

Bowen, T. et al., 2010 International consensus algorithm for the diagnosis, therapy and management of hereditary angioedema, Allergy, Asthma & Clinical Immunology, 6(24):1-13 (2010).

Bowen, T., Hereditary angioedema: beyond international consensus—circa Dec. 2010—The Canadian Society of Allergy and Clinical Immunology Dr. David McCourtie Lecture, Allergy, Asthma & Clinical Immunology, 7(1):1-14 (2011).

Brackertz, D. & Kueppers, F., Hereditary angioneurotic oedema, 302(7830) LANCET 680 (1973).

Bygum, A., Hereditary Angioedema—Consequences of a New Treatment Paradigm in Denmark, Acta Derm Venerol, 94:436-441 (2014).

Caballero, T. et al., Consensus Statement on the Diagnosis, Management, and Treatment of Angioedema Mediated by Bradykinin. Part II. Treatment, Follow-up, and Special Situations, J Investig Allergol Clin Immunol, 21(6):422-441 (2011).

Castellano, G. et al., Endothelial-To-Mesenchymal Transition in Swine Renal Ischemia Reperfusion Injury is Mediated by Complement and AKT Pathway, Nephrology Dialysis Transplantation, 27(2):ii1-ii2 (2012).

Caspi et al. (2010). P&T, vol. 35, Issue 7, Jul. 2010, Product Profiler: Berinert™.

Castellano, G. et al., Therapeutic Targeting of Classical and Lectin Pathways of Complement Protects from Ischemia-Reperfusion-Induced Renal Damage, The American Journal of Pathology, 176(4):1648-1659 (2010).

Choi, G. et al., Recombinant human C1-inhibitor in the treatment of acture angioedema attacks, Transfusion Practice, 47:1028-1032 (2007).

Cicardi, M. et al., Evidence-based recommendations for the therapeutic management of angioedema owing to hereditary C1 inhibitor (56) References Cited

OTHER PUBLICATIONS deficiency: consensus report of an International Working Group, European Journal of Allergy and Clinical Immunology, 67:147-157 (2011).
Cinryze® approval letter, FDA, Oct. 10, 2008, available at https://www.fda.gov/biologicsbloodvaccines/bloodbloodproducts/approvedproducts/licensedproductsblas/fractionatedplasmaproducts/ucm093602.htm (downloaded on May 25, 2017).
"Cinryze (C1-esterase Inhibitor) Developed by Lev Approved to Launch in the U.S.", Progress in Pharmaceutical Sciences, 33 (4), Dec. 31, 2009.
Cinryze® FDA Briefing Document, Blood Products Advisory Committee Meeting, May 1-2, 2008, available at https://www.fda.gov/ohrms/dockets/ac/08/briefing/2008-4355B2-1b.htm (downloaded on May 23, 2017).
Cinryze® Prescribing Information, ViroPharma Incorporated, Nov. 2012. ("Cinryze® label").
ClinicalTrials.gov Identifier: NCT01912456, A Study to Evaluate the Clinical Efficacy and Safety of Subcutaneously Administered C1-esterase Inhibitor in the Prevention of Hereditary Angioedema, (received Jul. 29, 2013), available at https://clinicaltrials.gov/ct2/show/NCT01912456 (downloaded on May 25, 2017).
ClinicalTrials.gov Identifier: NCT00748202, Berinert® P Study of Subcutaneous Versus Intravenous Administration (PASSION), (Sep. 4, 2008), available at https://clinicaltrials.gov/ct2/show/NCT00748202 (downloaded on Feb. 19, 2016).
ClinicalTrials.gov Identifier: NCT01756157, Subcutaneous CINRYZE With Recombinant Human Hyaluronidase for Prevention of Angioedema Attacks, (Jun. 29, 2012), available at https://clinicaltrials.gov/ct2/show/NCT01756157 (downloaded on May 25, 2017).
Connolly, B. D. et al., Weak Interactions Govern the Viscosity of Concentrated Antibody Solutions: High-Throughput Analysis Using the Diffusion Interaction Parameter, 103 BIOPHYS. J. 69-78 (Jul. 2012).
Craig, Curriculum Vitae of Dr. Timothy Craig, D.O.
Craig, Declaration of Dr. Timothy Craig.
Craig, T. et al., WAO Guideline for the Management of Hereditary Angioedema, WAO Journal, 182-199 (2012).
Craig, T. et al., When is prophylaxis for hereditary angioedema necessary?, Annals of Allergy, Asthma & Immunology, 102:366-372 (2009).
Cruz, M.P., Conestat Alfa (Ruconest) First Recombinant C1 Esterase Inhibitor for the Treatment of Acute Attacks in Patients with Hereditary Angioedema, Pharmacy and Therapeutics, 40(2):109-111, 114 (2015).
*CSL Behring GmbH and CSL Behring LLC*, Petitioners v. *Shire Viropharma Inc.*, Patent Owner, Petition for Inter Partes Review, U.S. Pat. No. 9,616,111, filed May 31, 2017, pp. 1-79.
CSL Behring Press Release dated May 3, 2012: "CSL Behring Initiates Study of Subcutaneous Administration of C1-esterase Inhibitor in Patients With Hereditary Angioedema".
CSL Ltd. Half Year Update 2016-2017, signed by John Shine, Apr. 2017, available at http://www.csl.com.au/docs/954/57/CSL_HYR17_sec.pdf.
D'Agnilo F. "Summary Basis for Regulatory Action—Cinryze" FDA. Published Oct. 9, 2008.
Davis, A.E. III, New treatments addressing the pathophysiology of hereditary angioedema, Clinical and Molecular Allergy, 6(2):1-7 (2008).
Dec. 2012 Update to Clinical Trial NCT01756157, Subcutaneous Cinryze With Recombinant Human Hyaluronidase for Prevention of Angioedema Attacks, (Dec. 24, 2012), available at https://clinicaltrials.gov/archive/NCT01756157/2012_12_24 (downloaded on May 25, 2017).
European Medicines Agency, Jun. 24, 2010, EMA/CHMP/450053/2010, Evaluation of Medicines for Human Use, CHMP Assessment Report, Ruconest®, Procedure No. EMEA/H/C/001223, available at http://www.ema.europa.eu/docs/en_GB/document_library/EPAR_-_Public_assessment_report/human/001223/WC500098546.pdf.

European Patent Application No. 14762343.3, Shire Reply dated Mar. 2, 2017.
European Search Report for EP14762343.3, 9 pages (dated Jan. 28, 2016).
Excerpt from ClinicalTrials.gov archive (dated Apr. 11, 2012) for NCT01576523.
Extract from "Ansel's Pharmaceutical Dosage Forms and Drug Delivery Systems"; ninth edition; 2001; Chapter 5, pp. 162-170; Eds. Allen Jr. et al.
Farkas, H. et al., Short-term prophylaxis in hereditary angioedema due to deficiency of the C1-inhibitor—a long-term survey, Allergy, 67:1586-1593 (2012).
Farkas, H., Pediatric hereditary angioedema due to C1-inhibitor deficiency, Allergy, Asthma & Clinical Immunology, 6(18):2-10 (2010).
Farrell, C. et al., Population pharmacokinetics of recombinant human C1 inhibitor in patients with hereditary angioedema, British Journal of Clinical Pharmacology, 76:897-907 (2013).
Fay, A. and Abinun, M., Current management of hereditary angiooedema (C'1 esterase inhibitor deficiency), J Clin Pathol, 55:266-270 (2002).
Feussner, etal. (2014). Biochemical comparison of four commercially available C1 esterase inhibitor concentrates for treatment of hereditary angioedema. Transfusion 54: 2566-2573. Oct. 2014.
Firszt, R. & Frank, M. M., An Overview of Novel Therapies for Acute Hereditary Angioedema, 11(6) Am. J. Clin. Dermatol. 383-88 (2010).
Frank, M. M. Declaration of Michael M. Frank, excerpted from the prosecution history of U.S. Pat. No. 9,616,111.
Frank, M.M., Recombinant and Plasma-Purified Human C1 Inhibitor for the Treatment of Hereditary Angioedema, WAO Journal, S29-S33 (2010).
Gatlin, L. A. & Brister Gatlin, C. A., Formulation and Administration Techniques to Minimize Injection Pain and Tissue Damage Associated with Parenteral Products, Chapter 17 in Injectable Drug Development Techniques to Reduce Pain and Irritation 401-21 (Pramod K. Gupta & Gayle A. Brazeau, eds., CRC Press 1999). ("Gatlin").
GenBank: CAA30314.
Gesuete, R. et al., Recombinant C1 Inhibitor in brain ischemic injury, Annals of Neurology, 66(3):332-342 (2009).
Ghannam, A. et al., C1 Inhibitor as a glycoprotein: The influence of polysaccharides on its function and autoantibody target, 71 Mol. Immunol. 161-65 (2016).
Ghazi, A. and Grant, J.A., Hereditary angioedema: epidemiology, management, the role of icatibant, Biologics: Targets and Therapy, 7:103-113 (2013).
Giatlin et al., "Formulation and Administration Techniques to Minimize Injection Pain and Tissue Damage Associated with Parenteral Products," extract from "*Injectable Drug Development. Techniques to Reduce Pain and irritation*"; Chapter 17.
Gomella, L. G. & Haist, S. A., Clinician's Pocket Reference (McGraw-Hill Professional 9th ed. 2002).
Gower, R.G. et al., Hereditary Angioedema cause by C1-Esterase Inhibitor Deficiency: A Literature-Based Analysis and Clinical Commentary on Prophylaxis Treatment Strategies, World Allergy Organization Journal, 4(2): S9-S21 (2011).
Gurewich, V. et al., Recombinant human C1-inhibitor prevents non-specific proteolysis by mutant pro-urokinase during optimal fibrinolysis, Thrombosis and haemostasis, 102(2):279-286 (2009) (abstract only).
Hack, C.E. et al., Target levels of functional C1-inhibitor in hereditary angioedema, Allergy, 67:123-130 (2012).
Hack, E. et al., Immuno-Safety of Recombinant Human C1 Inhibitor in Patients With Hereditary Angioedema: An Integrated Analysis, World Allergy Organization, S45 (2012).
Harrison, R.A., Human C1 Inhibitor: Improved Isolation and Preliminary Structural Characterization, 22 BIOCHEMISTRY 5001-07 (1983).
Hofstra, J.J. et al., Pharmacokinetics, clinical efficacy and safety of C1 inhibitor concentrate (C1-esteraseremmer-N) for treatment of hereditary (and acquired) angioedema, Academic Medical Centre Amsterdam, Sanquin Division of Plasma Products, 43.

(56) References Cited

OTHER PUBLICATIONS

Hofstra, J. J. et al., Pharmacokinetics, Clinical Efficacy and Safety of Plasma-Derived Nanofiltered C1 Inhibitor Concentrate for Treatment of Hereditary and Acquired Angioedema, Blood. 112(11):694-694 (2008).
Hollingsworth, C., Dyax Pushes Toward Front of Race for HAE Therapy, Bioworld Today, (Sep. 25, 2008) <http://search.proquest.com/professional/docview/1079003946?ac>.
Hossler, P. et al., Optimal and consistent protein glycosylation in mammalian cell culture, 19(9) GLYCOBIOLOGY 936-49 (2009).
Informed Consent Form for Enrollment for Adults (dated Apr. 20, 2012), for Study No. CSL839_2001, corresponding to ClinicalTrials.gov (National Institutes of Health) identification No. NCT01576523.
International Search Report for PCT/US2014/030309, 5 pages (dated Nov. 7, 2014).
Jiang, H. et al., Subcutaneous infusion of human C1 inhibitor in swine, Clinical Immunology, 136:323-328 (2010).
Jiang, H. et al., Subcutaneous (SQ) versus intravenous (IV) infusion of C1 Inhibitor (inh) on blood levels in swine, 6th C1 Inhibitor Deficiency Workshop 46 (May 2009).
Johann Wolfgang Goethe University Hospitals, Berinert P Study of Subcutaneous Versus Intravenous Administration (PASSION), ClinicalTrials.gov—NCT00748202, (2011).
Jolles, S. et al., New Frontiers in Subcutaneous Immunoglobulin Treatment, 1(1) Biol Ther 1-15 (2011).
Karadi, et at, 5th C1 Inhibitor Deficiency Workshop, 1-80 (May 31-Jun. 3, 2007).
Kawalec, P. et al., Administration of conestat alfa, human C1 esterase inhibitor and icatibant in the treatment of acute angioedema attacks in adults with hereditary angioedema due to C1 esterase inhibitor deficiency. Treatment comparison based on systematic review results, Pneumonol Alergol Pol, 81:95-104 (2013) (abstract only).
Koles, K. et al., Influence of lactation parameters on the N-glycosylation of recombinant human C1 inhibitor isolated from the milk of transgenic rabbits, Glycobiology, 14(11):979-986 (2004).
Koles, K. et al., N- and O-glycans of recombinant human C1 inhibitor expressed in the milk of transgenic rabbits, Glycobiology, 14(1):51-64 (2004).
Kreuz, J, Berinert P Study of Subcutaneous Versus Intravenous Administration (PASSION) ClinicalTrials.gov NCT00748202, published Sep. 4, 2008.
Latypov, R. F. et al., Elucidation of Acid-induced Unfolding and Aggregation of Human Immunoglobulin IgG1 and IgG2 Fc, 287 J. Biol. Chem. 1381-96 (2012).
Le Bas-Bernardet, S. et al., Xenotransplantation of Galactosyl-Transferase Knockout, CD55, CD59, CD39, and Fucosyl-Transferase Transgenic Pig Kidneys Into Baboons, Transplantation Proceedings, 43:3426-3430 (2011).
Levi, M. et al., Self-administration of C1-inhibitor concentrate in patients with hereditary or acquired angioedema caused by C1-inhibitor deficiency, 117 J. Allergy Clin. Immunol. 904-08 (2006). ("Levi").
Lev Pharmaceuticals, Inc, Clinical Pharmacology Review, Division of Hematology Office of Blood Review & Research, 1-8 (Dec. 4, 2007).
Li, H. H., Declaration of Dr. Huamin Henry Li (dated May 12, 2015).
Li, H. H., Self-administered C1 esterase inhibitor concentrates for the management of hereditary angioedema: usability and patient acceptance, 10 Patient Preference and Adherence 1727-37 (2016).
Lis, H. & Sharon, N., Protein glycosylation Structural and functional aspects, 218 Eur. J. Biochem. 1-27 (1993).
Longhurst, H. J. et al., C1L inhibitor concentrate home therapy for hereditary angioedema: a viable, effective treatment option, 147(1) Clin. Exp. Immunol. 11-7 (2007).
Longhurst, H. J. et al, HAE international home therapy consensus document, 6(22) Allergy Asthma Clin. Immunol. 1-7 (2010).

Longhurst, H. J. et al., Prevention of Hereditary Angioedema Attacks with a Subcutaneous C1 Inhibitor, 376(12) N. Engl. J. Med. 1131-40 (2017).
Longhurst, H., Rhucin, a recombinant C1 inhibitor for the treatment of hereditary angioedema and cerebral ischemia, Current Opinion in Investigational Drugs, 9(3):310-323 (2008).
Lucca, J.J.D. et al., Effects of C1 Inhibitor on Tissue Damage in a Porcine Model of Controlled Hemorrhage, Shock, 38(1):82-91 (2012).
Lumry, W. et al., Nanofiltered C1-Esterase Inhibitor for the Actute Management and Prevention of Hereditary Angioedema Attacks due to C1-Inhibitor Deficiency in Children, The Journal of Pediatrics, 162(5):1017-1022 (2013).
Machinig, T. and Waldhauser, H., Declaration of Dr. Thomas Machinig and Hanno Waldhauser.
Mahmood, I, Clinical Pharmacology Review, Published Dec. 4, 2007.
Martinez-Saguer et al., Pharmacokinetic Berinert P Study of Subcutaneous Versus Intravenous Administration in Subjects with Moderate Hereditary Angioedema—The Passion Study, 127 Allergy Clin. Immunol. AB104 (Feb. 2011) (Abstract 389).
Martinez-Saguer, I. et al., Pharmacokinetic Berinert P study of subcutaneous versus intravenous administration in subjects with moderate hereditary angioedema—the passion study, Journal of Allergy and Clinical Immunology, 127: AB104 (2011).
Martinez-Saguer, I. et al., Pharmacokinetics of plasma-derived C1-esterase inhibitor after subcutaneous versus intravenous administration in subjects with mild or moderate hereditary angioedema: the PASSION study, TRANSFUSION, 54:1552-1561 (2014).
Material Safety Data Sheet (MSDS) for Berinert® with a date of issue of Sep. 23, 2009.
Maurer, M. and Magerl, M., Long-term prophylaxis of hereditary angioedema with androgen derivates: a critical appraisal and potential alternatives, JDDG, 9:99-107 (2011).
Metzner, Curriculum Vitae of Dr. Hubert Metzner, Ph.D.
Metzner, Declaration of Dr. Hubert Metzner.
Myers, J. K. et al., Denaturant m values and heat capacity changes: Relation to changes in accessible surface areas of protein unfolding, 4 Protein Sci. 2138-48 (1995).
Moldovan, D. et al., Efficacy and safety of recombinant human C1-inhibitor for the treatment of attacks of hereditary angioedemas: European open-label extension study, Clinical & Experiential Allergy, 42(6):929-935 (2012) (abstract only).
Monkos, K., Concentration and temperature dependence of viscosity in lysozyme aqueous solutions, 1339 Biochimica Et Biophysica Acta 304-10 (1997).
Monkos, K., Viscometric study of human, bovine, equine and ovine haemoglobin in aqueous solution, 16(1) Int. J. Biol. Macromol. 31-5 (1994).
Monkos, K., Viscosity analysis of the temperature dependence of the solution conformation of ovalbumin, 85 Biophysical Chemistry 7-16 (2000).
Monkos, K., Viscosity of bovine serum albumin aqueous solutions as a function of temperature and concentration, 18 Int. J. Biol. Macromol. 61-8 (1996).
Nadeau et al. Cowen Biotechnology Report, Oct. 2010.
NewsRx, Parental Infusions; Studies from Duke University, Department of Pediatrics parenteral infusions, ProQuest Newsstand Professional, (Sep. 4, 2010) <http://search.proquest.com/professional/docview/746811428?acc>.
Nilsson, T. & Wiman, B., Purification and Characterization of Human C1-Esterase Inhibitor, 705 Biochim. Biophys. Acta 271-76 (1982).
Nzeako, U.C., Diagnosis and management of angioedema with abdominal involvement: A gastroenterology perspective, World J Gastroenterol, 16(39):4913-4921 (2010).
Over, J. et al., C1-Inhibitor, Chapter 17 in Production of Plasma Proteins for Therapeutic Use, 241-58 (Joseph Bertolini et al., eds., John Wiley & Sons, Inc. 2013).
Perkins, S.J. et al., Two-Domain Structure of the Native and Reactive Centre Cleaved Forms of C1 Inhibitor of Human Complement by Neutron Scattering, 214 J. Mol. Biol. 751-63 (1990).

(56) References Cited

OTHER PUBLICATIONS

Pharming Technologies B.V., Recombinant Human C1 Inhibitor for the Treatment of Acute Attacks in Patients with Hereditary Angioedema, ClinicalTrials.gov—NCT00225147, (2005).
Poster presented in Mar. 2012 and entitled "Safety, Pharmacokinetics (PK), and Pharrnacodynamics (PD) of Subcutaneous (SC) Cinryze® (C1 Esterase Inhibitor [Human]) with Recombinant Human Hyaluronidase (rHuPH20) in Subjects with Hereditary Angioedema (HAE)" (p. 1 is the entire poster, pp. 2 to 4 are enlargements of portions of p. 1).
Pragst, Declaration of Ingo Pragst dated Dec. 15, 2016, filed in Observations in Great Britain application No. GB1519921.9.
Press release by BMI Research dated Mar. 6, 2012 "Subcutaneous Cinryze® with rHuPH20 Produces Positive Effects in Prevention of HAO".
Press Release, CSL Behring, CSL Behring announces completion of national marketing authorizations of Berinert® after MRP in 23 European countries (May 27, 2010), available at http://www.cslbehring.com/s1/cs/enco/1255923338532/news/1255924303464/prdetail.htm?tabSelections=1255923338570¤ tPage=4 (downloaded on May 23, 2017).
Press Release, CSL Behring, CSL Behring Initiates Study of Subcutaneous Administration of C1-esterase inhibitor in Patients with Hereditary Angioedema (May 3, 2012), available at http://www.cslbehring.com/news-room/Study-of-C1-INH-as- SubQ-Formulation (downloaded on Jan. 10, 2017).
Press Release, Roche, Roche's Herceptin given by subcutaneous injection offers greater convenience to patients and reduces overall healthcare costs compared to standard IV infusion (Mar. 23, 2012) available at http://www.roche.com/media/store/releases/med-cor-2012-03- 23.htm.
Press Release, ViroPharma Inc., ViroPharma and Halozyme Therapeutics Announce Initiation of Phase 2b Dose Ranging Combination Study for Subcutaneous Administration of Cinryze® (C1 esterase inhibitor [human]) With Hyaluronidase (rHuPH20) (Dec. 19, 2012) available at http://www.halozyme.com/investors/news-releases/news-release- details/2012/ViroPharma-and-Halozyme-Therapeutics-Announce-Initiation-of-Phase-2b-Dose-Ranging-Combination-Study-for-Subcutaneous-Administration-of-Cinryze-C1-esterase-inhibitor-human-With-Hyaluronidase-rHuPH20/default.aspx (downloaded on Feb. 19, 2016).
Press Release, ViroPharma Inc., ViroPharma Announces Completion of Enrollment in Phase 2 Study Evaluating Subcutaneous Delivery of Cinryze® (C1 Esterase Inhibitor [Human]), (Oct. 25, 2010) available at http://www.prnewswire.com/news-releases/viropharma- announces-completion-of-enrollment-in-phase-2-study- evaluating-subcutaneous-delivery-of-cinryze-c1-esterase-inhibitor-human-105666398.html (downloaded on Mar. 20, 2017).
Press Release, ViroPharma Inc., ViroPharma Provides Update on Phase 2 Clinical Evaluation of Subcutaneous Cinryze® (C1 esterase inhibitor [human]) with Recombinant Human Hyaluronidase (rHuPH20) (Aug. 1, 2012) available at http://www.prnewswire.com/news-releases/viropharma-provides- update-on-phase-2-clinical-evaluation-of-subcutaneous-cinryze- c1-esterase-inhibitor-human-with-recombinant-human- hyaluronidase-rhuph20-164636346.html (downloaded on May 25, 2017).
Prosecution History of U.S. Pat. No. 9,616,111.
Protest and Submission of Prior Art Submitted in Canadian Patent Application No. 2,904,543, filed Sep. 27, 2017.
R & D Focus Drug News, CSL Behring phase change I/II. USA (angioedema), IMSworld Publications Ltd., (Jun. 14, 2012) <http://search.proquest.com/professional/docview/1020661991?ac>.
R & D Focus Drug News, recombinant human C1 esterase inhibitor, Pharming Pharming submitted (angioedema), IMSworld Publications Ltd., (Jul. 31, 2006) <http://search.com/professional/docview/670195890?ac>.
R & D Focus Drug News, recombinant human C1 esterase inhibitor, Pharming Pharming Fast Track, USA (angioedema), IMSworld Publications Ltd., (Aug. 7, 2006) <http://search.proquest.com/professional/docview/771275903?accou>.

Relan, A. et al., Recombinant C1-Inhibitor Effects on Coagulation and Fibrinolysis in Patients with Hereditary Angioedema, Biodrugs, 26(1):43-52 (2012).
Research & Development Slides, CSL Behring, Dec. 6, 2012.
Reshef, A. et al., Clinical Efficacy of Recombinant Human C1 Inhibitor in Patients with Acute Hereditary Angioedema Attacks, World Allergy Organization, S45 (2012).
Reshef, A. et al., Recombinant human C1 inhibitor for the prophylaxis of hereditary angioedema attacks: a pilot study, Allergy, 68:118-124 (2013).
Reuter, G. & Gabius, H.-J., Eukaryotic glycosylation: whim of nature or multipurpose tool?, 55 CMLS, Cell. Mol. Life Sci. 368-422 (1999).
Riedl, M. A. et al., Subcutaneous administration of human C1 inhibitor with recombinant human hyaluronidase in patients with hereditary angioedema, 37(6) Allergy Asthma Proc. 489-500 (2016).
Roberts, C. J., Declaration of Dr. Christopher J. Roberts.
Roberts, C. J., Curriculum Vitae of Dr. Christopher J. Roberts, Ph.D.
Rossi, V. et al., Functional Characterization of the Domain: Insights into Heparin Binding Recombinant Human C1 Inhibitor Serpin, J. Immunol, 184: 4982-4989 (2010).
Sanquin, Scientific Report, Blood and Beyond, 1-226 (2007).
Sardana, N. & Craig, T. J., Recent Advances in Management and Treatment of Hereditary Angioedema, 128(6) Pediatrics 1173-80 (2011).
Schellekens, H., Why some proteins have sugars? Epoetins, from alfa to zeta, 14(6) EJHP Practice 29-35 (2008).
Schrantz, Declaration of Dr. Jennifer Schrantz dated Sep. 15, 2015, including Exhibit B referred to in that Declaration (obtained from USPTO online file of U.S. Appl. No. 14/855,168).
Schrantz, Declaration of Dr. Jennifer Schranz, excerpted from the prosecution history of U.S. Pat. No. 9,616,111.
Schrantz et al. (2012). J Allergy Clin Immunology 129(2), AB369, Abstract L21.
Schrantz et al. (2012). Poster presented at American Academy of Allergy, Asthma & Immunology Annual Meeting, Orlando FL, Mar. 2-Mar. 6, 2012.
Schranz, J. et al., Safety, Pharmacokinetics (PK), and Pharmacodynamics (PD) of Subcutaneous (SC) CINRYZE® (C1 Esterase Inhibitor [Human])with Recombinant Human Hyaluronidase (rHuPH20) in Subjects with Hereditary Angioedema (HAE), ViroPharma Incorporated, Poster L21 presented at the 2012 American Academy of Allergy, Asthma & Immunology annual meeting. ("Schranz").
Schreiber et al. (1973). Inhibition by C1INH of Hageman Factor Fragment Activation of Coagulation, Fibrinolysis, and Kinin Generation, J.Clin. Inv. 52: 1402-1409.
Shalaev, E. Y. et al., Thermophysical properties of pharmaceutically compatible buffers at sub-zero temperatures: implications for freeze-drying, 19(2) Pharmaceutical Res. 195- 201 (2002).
Shire, S.J., Formulation and manufacturability of biologics, 20 Current Opinion in Biotechnology, 708-14 (2009).
Solá, R. J. and Griebenow, K., Effects of Glycosylation on the Stability of Protein Pharmaceuticals, 98(4) J. Pharm. Sci. 1223-45 (2009).
Späth, P.J. et al., Quantification of C1-Inhibitor Functional Activities by Immunodiffusion Assay in Plasma of Patients with Hereditary Angioedema—Evidence of a Functionally Critical Level of C1-Inhibitor Concentration, 1 Complement 147-59 (1984).
Strengers, P., Sanquin, C1 -Esteraseremmer-N for the Treatment of Hereditary (and Acquired) Angioedema, ClinicalTrials.gov Identifier: NCT00125541, 4 pages (Jul. 29, 2005).
Subcutaneous CINRYZE with Recombinant Human Hyaluronidase for Prevention of Angioedema Attacks, https://clinicaltrials.gov/ct2/show/results/NCT01756157?term=NCT01756157&rank=1, Accessed Mar. 23, 2016.
Tillou, X. et al., Recombinant human C1-inhibitor prevents acute antibody-mediated rejection in alloimmunized baboons, Kidney International, 78: 152-159 (2010).
Van Doorn, M.B.A. et al., A phase I study of recombinant human C1 inhibitor in asymptomatic patients with hereditary angioedema (HAE), Br J Clin Pharmacol, 59(1):136 (2004).

(56) References Cited

OTHER PUBLICATIONS

Van Doorn, M.B.A. et al., A phase I study of recombinant human C1 inhibitor in asymptomatic patients with hereditary angioedema, J. Allergy Clin. Immunol., 116(4): 876-883 (2005).
United Kingdom Patent Application No. 1519921.9, Shire Reply dated Mar. 2, 2017.
United States Securities and Exchange Commission, Form 10-K for the fiscal year ended Dec. 31, 2012, ViroPharma Inc.
United States Securities and Exchange Commission, Form 10-Q for the quarterly period ended Jun. 30, 2011, ViroPharma Inc.
United States Securities and Exchange Commission, Form 10-Q for the quarterly period ended Jun. 30, 2013, ViroPharma Inc.
ViroPharma Incorporated, Cinryze, Presentation, 76 pages (Mar. 19, 2010).
Vivaglobin® Prescribing Information, CSL Behring, Apr. 2010.
Wahn, V. et al., Hereditary angioedema (HAE) in children and adolescents—a consensus on therapeutic strategies, European Journal of Pediatrics, 171: 1339-1348 (2012).
Wang, W., Protein Aggregation and Its Inhibition in Biopharmaceutics, 289 Int. J. Pharm. 1-30 (2005).
WC500098546, CHMP assessment report, European Medicines Agency, EMA/CHMP/450053/2010, (Jun. 24, 2010).
WC500103884, Cinryze C1 inhibitor, human, European Medicines Agency, EMA/CHMP/217963/2011 (Mar. 17, 2011).
WC500108895, Annex 1 Summary of Product Characteristics, 1-33.
WC500108896, Appendix, EU/1/11/688/001.
WC500108897, Annex Conditions or Restrictions with Regard to the Safe and Effective Use of the Medicinal Product to be Implemented by the Member States, 1-3.
WC500108898, Assessment Report Cinryze, EMEA/H/C/001207.
WC500108899, Cinryze C1 inhibitor (human), EMA/244001/2011 and EMEA/H/C/001207.
WC500142079, Cinryze (C1 Inhibitor (human)), European Medicines Agency, EMA/175539/2013, (Feb. 21, 2013).
Weiss IV, W. F. et al., Principles, Approaches, and Challenges for Predicting Protein Aggregation Rates and Shelf Life, 98(4) J. Pharm. Sci. 1246-77 (2009).
Wolff, M.W. et al., Expression of C1 esterase inhibitor by the baculovirus expression vector system: preparation, purification, and characterization, Protein Expression and Purification, 22(3):414-421 (2001).
Vugmeyster et al., "Pharmacokinetics and toxicology of therapeutics: advances and challenges," World J. Biol. Chem. 3:73-92. Published Apr. 26, 2012.
Yadav, S. et al., Viscosity Analysis of High Concentration Bovine Serum Albumin Aqueous Solutions, 28 Pharm. Res. 1973-83 (2011).
Zuraw, B. L. et al., Nanofiltered C1 Inhibitor Concentrate for Treatment of Hereditary Angioedema, 363(6) N. Engl. J. Med. 513-22 (2010). ("Zuraw").
Zuraw, B. L. et al. Phase II study results of a replacement therapy for hereditary angioedema with subcutaneous C1-inhibitor concentrate, 70 Allergy 1319-28 (2015).
Zuraw, B.L. et al., Recombinant human C1-inhibitor for the treatment of acute angioedema attacks in patients with hereditary angioedema, J. Allergy Clin. Immunol., 126(4): 821-827 (2010).
Zuraw, B.L., HAE therapies: past present and future, Allergy, Asthma & Clinical Immunology, 6(23): 1-8 (2010).
Zuraw, Hereditary Angioedema, N Engl J Med, 359(10):1027-1036 (2008).
Jiang et al., "Subcutaneous infusion of human C1 inhibitor in swine", Clinical Immunology, 2010; 136: 323-328.
The Pharmaceutics and Compounding Laboratory (2010); "Subcutaneous"; UNG; http://pharmlabs.unc.edu/labs/parenterals/subcutaneous.htm.
Extract from "Ansel's Pharmaceutical Dosage Forms and Drug Delivery Systems"; ninth edition; 2001; Chapter 5, pp. 162-170.
Poster entitled "Safety, Pharmacokinetics (PK), and Pharmacodynamics (PD) of Subcutaneous (SC) Ginryze® (C1 Esterase Inhibitor [Human]) with Recombinant Human Hyaluronidase (rHuPH20) in Subjects with Hereditary Angioedema (HAE)" (p. 1 is the poster, pp. 2-3 are enlargements of p. 1 and p. 3 is an enlargement of Figure 1 of the poster).
Publication of the abstract L21 in J Allergy Cun Mmunol, vol. 129, No. 2 (Feb. 2012).
Press Release by BMI Research on Mar. 6, 2012.
Austria Codex Fachinformation 1997/1998, pp. 355-366 (Berinert P).
Lunn et al., "Cinryze™ as the first approved C1 inhibitor in the USA for the treatment of hereditary angioedema: approval, efficacy and safety", Journ. Blood Medicine, 2010; 1; 163-170.
CSL Behring® —Hizentra—Zusammenfassung der Merkmale des Arzneim ittels.
Poster entitled "Comparison of the viscosity of three subcutaneous immunoglobulin brands (SCIG) Potential implications in clinical use" by Haag et al. presented at the occasion of the XIIth Meeting of the ESID, Oct. 4-7, 2006, Budapest, Hungary.
Drouet et al., "A sensitive method to assay blood complement C1 Inhibitor activity", Clinica Chimica Acta, 1988; 174; 121-130.
Cardona et al., "Recent developments in the treatment of acute abdominal and facial attacks of hereditary angioedema: focus on human C1 esterase inhibitor", The Application of Clinical Genetics, 2010: 3; 133-146.
Burckbuchler et al., "Rheological and syringeability properties of highly concentrated human polyclonal immunoglobulin solutions", European Journal of Pharmaceutics and Biopharmaceutics, 2010; 76 :351-356.
CINRYZE® Highlights of prescribing information.
European Pharmacopoeia Fourth Edition, Sep. 20, 2001 (Human Albumin Solution).
Austria Codex Fachinformation 1997/1998, pp. 354-355 and 1460-1461 (Beriglobin, Human Albumin).
De Serres et al., "Safety and efficacy of pasteurized C1 inhibitor concentrate (Berinert® P) in hereditary angioedema: a review", Transfusion and Apheresis Science, 2003, 29: 24 7-254.
Craig declaration and exhibits (Annex A: Haegarda® Prescribing Information ; Annex B: Web page for the CSL Behring trial CSL830 2001 NCT01576523 Annex C: Informed Consent Form; Annex D: Informed Consent Form (signed by a patient taking part in the trial: identity of patient has been masked); Annex E:Zuraw et al, 2015 (see E3)).
Informed Consent Form for enrolment of adults for CSL830 2001 clinical trial sponsored by CSL Behring : US site : Hershey Medical Center, Hershey, PA (signed by a patient taking part in the trial; identity of patient has been masked); Informed Consent Form for enrolment of adults for CSL830 2001 clinical trial sponsored by CSL Behring: Germany site: Johann Wolfgang Goethe University Hospital, Frankfurt, Germany.
Zuraw B.L., et al. (2015) Allergy, 1319-1328, *Phase II study results of a replacement therapy for hereditary angioedema with subcutaneous Ct-inhibitor concentrate*, including Supplementary Appendixes S1 and S2.
Clinical Trials web page from https://clinicaltrials.gov for the CSL Behring CSL830 2001 trial NCT01576523 as available on Jan. 18, 2013 at https://clinicaltrials.gov/archive/NCT01576523/2013_01_18.
Martinez-Saguer et al., Transfusion, vol. 54, Jun. 2014, p. 1552-1561 (Document "D18" in Examination proceedings): the PASSION study.
Schranz et al. abstract L21 in J Allergy Clin Mmunol, vol. 129, No. 2 (Feb. 2012) (Document D5a in Examination proceedings).
Schranz et al Poster entitled "*Safety, Pharmacokinetics (PK), and Pharmacodynamics (PD) of Subcutaneous (SC) Cinryze® (C1 Esterase Inhibitor [Human]) with Recombinant Human Hyaluronidase (rHuPH20) in Subjects with Hereditary Angioedema (HAE)*" presented on Tuesday Mar. 6, 2012 at the AAAAI meeting in Orlando, Florida, USA during the poster-session; Press Release by BMI Research on Mar. 6, 2012, in connection with the Poster.
Clinical Trials web page for study NCT01095497 as available on Mar. 7, 2012: https://clinicaltrials.gov/archive/NCT01095497/2012_03_07 and https://clinicaltrials.gov/archive/NCT01095497.
Cinryze: EMN602545/2013 "CHMP assessment report for paediatric use studies submitted according to Article 46 of the Regulation (EC)

(56) References Cited

OTHER PUBLICATIONS

N° 1901/2006", Jul. 25, 2013 available at http://www.ema.europa.eu/docs/en GB/document library/EPAR—Assessment Report—Variation/human/001207/WC500152686.pdf.
Product Information for Berinert® (version available as of 2012); Summary of Berinert® Product Characteristics (Germany); Berinert® Package Insert (United States).
Cinryze®: Summary of Product Characteristics (EMA) first published in Jul. 2011; current version available at: http://www.ema.europa.eu/ema/index.jsp?curl=pages/medicines/human/medicines/001207/human_med_001448.jps&mid=WC0b01ac058001d124.
Martinez-Saguer et al. (2011), Journal of Allergy & Clinical Immunology 127: AB104 (Passion Abstract).
Martinez-Saguer et al., Poster entitled "Pharmacokinetic Berinert® study of subcutaneous versus intravenous administration in patients with moderate hereditary angioedema—the PASSION study" presented at the AAAAI meeting in San Francisco in Mar. 2011.
Extract from WIPO on-line file for WO2014/145519 (PCT application underlying contested patent EP2968434)—PCT Request as initially filed.
Extract from WIPO on-line file for W02014/145519—1st request for correction of the applicant, from ViroPharma Incorporated to Shire Orphan and Rare Diseases GmbH.
Extract from WIPO on-line file for WO2014/145519—substituted sheets of the request, issued by WIPO.
Extract from WIPO on-line file for WO2014/145519—2nd request for correction of the applicant, from Shire Orphan and Rare Diseases GmbH to Viropharma Holdings Limited.
Extract from WIPO on-line file for WO2014/145519—substituted sheets of the request.
Extract from WIPO on-line file for WO2014/145519—Request for registering the assignment from Viropharma Holdings Limited to Shire Viropharma Incorporated.
Martinez-Saguer Declaration I and exhibits (Annex 1: Site-specific Informed Consent Form, Annex 2) (Google machine translation included).
Guide "Patienten in klinischen Studien" issued by VFA (Verband Forschender Arzneimittelhersteller). (Google machine translation included).
Zuraw et al (2010). Allergy, Asthma & Clinical Immunology, 2010, 6:23. "HAE Therapies: past present and future".
Extract from "Injectable Drug Development. Techniques to Reduce Pain and irritation"; 1999; Chapter 17; Gatlin et al. "Formulation and Administration techniques to minimize Injection Pain and Tissue Damage Associated with Parenteral Products".
Cardona et al (2010). The Application of Clinical Genetics 2010:3; 133-146. "Recent developments in the treatment of acute abdominal and facial attacks of hereditary angioedema: focus on human C1 esterase inhibitor".
Jiang et al (2010). Clinical Immunology 136, 323-328. "Subcutaneous infusion of human C1 inhibitor in swine".
CSL Behring Press Release, May 3, 2012. "CSL Behring Initiates Study of Subcutaneous Administration of C1-esterase inhibitor in Patients with Hereditary Angioedema".
Viropharma Incorporated Investor Day presentation, available at https://www.sec.gov/Archives/edgar /data/946840/000119312512399193/d414342dex991.htm, The slides were disclosed to the SEC as part of a Form 8-K; the lodging date of the 8-K and associated documents, and the 8-K form can be found at https://www.sec.gov/Archives/edgar/data/946840/000119312512399193/0001193125-12-399193-index.htm.
Infringement complaint filed by Shire Viropharma Incorporated, 300 Shire Way, Lexington, MA 02421, USA at the Munich Regional Court I on Jun. 26, 2017, against CSL Behring GmbH, Emil-von-BehringStrasse 76, 35041, Marburg, Germany, in relation to European patent EP 2 968 434. (Google machine translation included).
Martinez-Saguer Declaration II and exhibits (Annex 1: ClinicalTrials.gov extract for the PASSION Study; Annex 2: Poster presented at the AAAAI meeting in San Francisco in Mar. 2011 and abstract; Annex 3: Poster presented at the EAACI meeting in Istanbul in Jun. 2011 and abstract; Annex 4: Slide presentation presented at Budapest during a workshop in May 2011, and associated program).
Waldhauser declaration and exhibits (Exhibit A: Hanno Waldhauser's badge; Exhibit B: Meeting Summary; Exhibit C: Schranz poster; Exhibit D: Enlargement of Figure 1 of Schranz poster; Exhibit E: Photograph of Schranz poster; Exhibit F: Abstract of the Schranz poster; Exhibit G Viropharma and Halozyme Press Release, Mar. 6, 2012).
Martinez-Saguer et al. slide presentation ("Parmacokinetics of plasmaderived C1-esterase inhibitor after subcutaneous versus intravenous administration in patients with moderate hereditary angioedema"), presented in Budapest during a HAE workshop in May 2011.
Martinez-Saguer et al. Poster ("Parmacokinetics of plasma-derived C1-esterase inhibitor after subcutaneous versus intravenous administration in subjects with moderate hereditary angioedema"), presented at the EAACI meeting in Istanbul in Jun. 2011, and associated abstract.
FDA web page "Informed Consent for Clinical Trials" available at: https://www.fda.gov/forpatients/clinicaltrials/informedconsent/default.htm.
Program of Poster-Session of 2012 AAAAI meeting in Orlando, Florida, USA (Tuesday Mar. 6, 2012).
Viropharma Study Synopsis dated Sep. 6, 2011, made public on Shire's website after completion of ViroPharma acquisition in 2014 at http://www.shiretrials.com//media/files/clinical%20trials/clinicaltrialsen/clinical%20study%20reports/shire-0624-200-clinical-study-report-redact.pdf.
Herget declaration and exhibits (Exhibit A: clinical trial web page NCT01576523; Exhibit B: Site-specific Informed Consent form (Germany) ; Exhibit C: File note Parexel; Exhibit D: Monitoring plan Parexel for CSL830_2001 study, with sign-off sheet).
Nolte declaration and exhibit (Exhibit 1: Site-specific Informed Consent Form, Germany).
Van Doorn et al. (2005).J. Allergy Cli. Immunol. 116:4; 876-883. "A phase I study of recombinant human C1 inhibitor in asymptomatic patients with hereditary angioedema".
Tourangeau & Zuraw (2011). Curr. Allergy Asthma Rep 11:345-351. "The New Era of C1 Esterase Inhibitor Deficiency Therapy".
Shire S.J. et al. (Jun. 2004). J. Pharm. Sci. vol. 93, n°6, pp. 1390-1402. "Challenges in the Development of High Concentration Formulations".
Sola R.J. and Griebenow K. (2009). J Pharm Sci. 98(4):1223-45. "Effects of Glycosylation on the Stability of Protein Pharmaceuticals".
Bioonnews: CSL Behring Initiates Study of Subcutaneous Administration of C1-esterase Inhibitor in Patients with Hereditary Angioedema (Google machine translation included).
Opposition against European Patent No. EP2968434, filed by CSL Behring GmBH on Mar. 28, 2018.
Second Protest and Submission of Prior Art in Canadian Patent Application No. 2,904,543, filed on Apr. 16, 2018.
Petition for Inter Partes Review of U.S. Pat. No. 9,616,111, filed by CSL Behring GmbH and CSL Behring LLC on May 31, 2017.
Decision Denying Institution for Inter Partes Review of U.S. Pat. No. 9,616,111, entered on Dec. 7, 2017.
Opposition against European Patent No. EP2968434, filed by Octapharma AG on Mar. 28, 2018.
Infringement complaint filed by Shire Viropharma Incorporated, 300 Shire Way, Lexington, MA 02421, USA at the Munich Regional Court I on Jun. 26, 2017, against CSL Behring GmbH, Emil-von-BehringStrasse 76, 35041, Marburg, Germany, in relation to European patent EP 2 968 434.
English translation of: Infringement complaint filed by Shire Viropharma Incorporated, 300 Shire Way, Lexington, MA 02421, USA at the Munich Regional Court I on Jun. 26, 2017, against CSL Behring GmbH, Emil-von-BehringStrasse 76, 35041, Marburg, Germany, in relation to European patent EP 2 968 434.
English translation of: Martinez Saguer Declaration II and exhibits (Annex 1: ClinicalTrials.gov extract for the PASSION Study; Annex 2: Poster presented at the AAAAI meeting in San Francisco in Mar. 2011 and abstract; Annex 3: Poster presented at the EAACI meeting (56) References Cited

OTHER PUBLICATIONS in Istanbul in Jun. 2011 and abstract; Annex 4: Slide presentation presented at Budapest during a workshop in May 2011, and associated program).
English translation of: CSL Behring® —Hizentra—Zusammenfassung der Merkmale des Arzneim ittels.
Austria Codex Fachinformation 1997/1998, pp. 355, 356 and 469 (Berinert P).
English translation of: Austria Codex Fachinformation 1997/1998, pp. 355, 356 and 469 (Berinert P).
English translation of: Austria Codex Fachinformation 1997/1998, pp. 354-355 and 1460-1461 (Beriglobin, Human Albumin).
Informed Consent Form for enrollment of adults for CSL830 2001 clinical trial sponsored by CSL Behring : US site : Hershey Medical Center, Hershey, PA (signed by a patient taking part in the trial; identity of patient has been masked); Informed Consent Form for enrollment of adults for CSL830 2001 clinical trial sponsored by CSL Behring: Germany site: Johann Wolfgang Goethe University Hospital, Frankfurt, Germany.
English translation of: Informed Consent Form for enrollment of adults for CSL830 2001 clinical trial sponsored by CSL Behring : US site : Hershey Medical Center, Hershey, PA (signed by a patient taking part in the trial; identity of patient has been masked); Informed Consent Form for enrollment of adults for CSL830 2001 clinical trial sponsored by CSL Behring: Germany site: Johann Wolfgang Goethe University Hospital, Frankfurt, Germany.
Guide "Patienten in klinischen Studien" issued by VFA (Verband Forschender Arzneimittelhersteller).
English translation of: Guide "Patienten in klinischen Studien" issued by VFA (Verband Forschender Arzneimittelhersteller).
Martinez Saguer Declaration I and exhibits (Annex 1: Site-specific Informed Consent Form, Annex 2).
English translation of: Martinez Saguer Declaration I and exhibits (Annex 1: Site-specific Informed Consent Form, Annex 2).
English translation of: Nolte declaration and exhibit (Exhibit 1: Site-specific Informed Consent Form, Germany).
English translation of: Herget declaration and exhibits (Exhibit A: clinical trial web page NCT01576523; Exhibit B: Site-specific Informed Consent form (Germany) ; Exhibit C: File note Parexel; Exhibit D: Monitoring plan Parexel for CSL830_2001 study, with sign-off sheet).
Patient information on the clinical study: "Prostate and lymphatic flow radiation with integrated boost IMRT after neoadjuvant hormonal therapy" PLATIN, Therapy arm PLAT1N-4.
English translation of: Patient information on the clinical study: "Prostate and lymphatic flow radiation with integrated boost IMRT after neoadjuvant hormonal therapy" PLATIN, Therapy arm PLAT1N-4.
VFA. Die forschenden Pharma-Untemehmen "The path to a new drug".
English translation of: VFA. Die forschenden Pharma-Untemehmen "The path to a new drug".
Extract European and German Patent Register (EP 2 968 434) cited as Exhibit LL01 in the Infringement complaint filed by Shire Viropharma Incorporated, at the Munich Regional Court I on Jun. 22, 2017, against CSL Behring GmbH, in relation to European patent EP 2 968 434. (English translation included).
Decision to grant the European Patent pursuant to Art. 97 (1) EPC cited as Exhibit LL02 in the Infringement complaint filed by Shire Viropharma Incorporated, at the Munich Regional Court I on Jun. 22, 2017, against CSL Behring GmbH, in relation to European patent EP 2 968 434.
Patent specification, claims and drawings (Communication pursuant to Rule 71 (3) EPC cited as Exhibit LL03 in the Infringement complaint filed by Shire Viropharma Incorporated, at the Munich Regional Court I on Jun. 22, 2017, against CSL Behring GmbH, in relation to European patent EP 2 968 434.
CSL press release re. US litigation dated Apr. 12, 2017 cited as Exhibit LL05 in the Infringement complaint filed by Shire Viropharma Incorporated, at the Munich Regional Court I on Jun. 22, 2017, against CSL Behring GmbH, in relation to European patent EP 2 968 434.
Shire entity details, State of Delaware cited as Exhibit LL06 in the Infringement complaint filed by Shire Viropharma Incorporated, at the Munich Regional Court I on Jun. 22, 2017, against CSL Behring GmbH, in relation to European patent EP 2 968 434.
Website extracts of CSL Behring cited as Exhibit LL07 in the Infringement complaint filed by Shire Viropharma Incorporated, at the Munich Regional Court I on Jun. 22, 2017, against CSL Behring GmbH, in relation to European patent EP 2 968 434. (English translation included).
Trade register excerpt of CSL Behring GmbH cited as Exhibit LL08 in the Infringement complaint filed by Shire Viropharma Incorporated, at the Munich Regional Court I on Jun. 22, 2017, against CSL Behring GmbH, in relation to European patent EP 2 968 434. (English translation included).
Meeting minutes of the analysts Seeking Alpha (regarding conference call Aug. 11, 2015) cited as Exhibit LL09 in the Infringement complaint filed by Shire Viropharma Incorporated, at the Munich Regional Court I on Jun. 22, 2017, against CSL Behring GmbH, in relation to European patent EP 2 968 434.
Meeting minutes between CSL Ltd. nad Analysts of S&P Capital IQ dated Nov. 30, 2016 cited as Exhibit LL10 in the Infringement complaint filed by Shire Viropharma Incorporated, at the Munich Regional Court I on Jun. 22, 2017, against CSL Behring GmbH, in relation to European patent EP 2 968 434.
Meeting minutes re. half-year result 2016 dated Feb. 14, 2017 cited as Exhibit LL11 in the Infringement complaint filed by Shire Viropharma Incorporated, at the Munich Regional Court I on Jun. 22, 2017, against CSL Behring GmbH, in relation to European patent EP 2 968 434.
Clinical study protocol CSL830_3001 cited as Exhibit LL14 in the Infringement complaint filed by Shire Viropharma Incorporated, at the Munich Regional Court I on Jun. 22, 2017, against CSL Behring GmbH, in relation to European patent EP 2 968 434.
ClinicalTrials.gov Study Protocol re. NCT02316353 cited as Exhibit LL15 in the Infringement complaint filed by Shire Viropharma Incorporated, at the Munich Regional Court I on Jun. 22, 2017, against CSL Behring GmbH, in relation to European patent EP 2 968 434.
CSL Behring press release dated Mar. 22, 2017 NEJM Publishes Pivotal Data on Preventing HAE Attacks cited as Exhibit LL16 in the Infringement complaint filed by Shire Viropharma Incorporated, at the Munich Regional Court I on Jun. 22, 2017, against CSL Behring GmbH, in relation to European patent EP 2 968 434.
Frankfurter Allgemeine Newspaper Article "Pharmaunternehmen baut Marburger Standort aus" (Pharma-Company expands Marburg place of business) cited as Exhibit LL17 in the Infringement complaint filed by Shire Viropharma Incorporated, at the Munich Regional Court I on Jun. 22, 2017, against CSL Behring GmbH, in relation to European patent EP 2 968 434. (English translation included).
CSL's manufacturer's authorization (EudraGMP) cited as Exhibit LL18 in the Infringement complaint filed by Shire Viropharma Incorporated, at the Munich Regional Court I on Jun. 22, 2017, against CSL Behring GmbH, in relation to European patent EP 2 968 434.
Press Article of Oberhessische Presse Online Feb. 23, 2017 "Sie nimmt der Krankheit ihre Macht; Kathrin Schön leidet an HAE" (She takes away the power from the disease; Kathrin Schön suffers from HAE) cited as Exhibit LL19 in the Infringement complaint filed by Shire Viropharma Incorporated, at the Munich Regional Court I on Jun. 22, 2017, against CSL Behring GmbH, in relation to European patent EP 2 968 434. (English translation included).
Extract Trade Mark Register re. HAEGARDA cited as Exhibit LL20 in the Infringement complaint filed by Shire Viropharma Incorporated, at the Munich Regional Court I on Jun. 22, 2017, against CSL Behring GmbH, in relation to European patent EP 2 968 434.
Map showing HAE-Patients living in Germany cited as Exhibit LL21 in the Infringement complaint filed by Shire Viropharma Incorporated, at the Munich Regional Court I on Jun. 22, 2017, (56) References Cited

OTHER PUBLICATIONS against CSL Behring GmbH, in relation to European patent EP 2 968 434. (English translation included).
List of HAE specialized treatment centres and doctors cited as Exhibit LL22 in the Infringement complaint filed by Shire Viropharma Incorporated, at the Munich Regional Court I on Jun. 22, 2017, against CSL Behring GmbH, in relation to European patent EP 2 968 434. (English translation included).
CSL job advertisement sales representatives cited as Exhibit LL23 in the Infringement complaint filed by Shire Viropharma Incorporated, at the Munich Regional Court I on Jun. 22, 2017, against CSL Behring GmbH, in relation to European patent EP 2 968 434. (English translation included).
Claim construction cited as Exhibit LL24 in the Infringement complaint filed by Shire Viropharma Incorporated, at the Munich Regional Court I on Jun. 22, 2017, against CSL Behring GmbH, in relation to European patent EP 2 968 434. (English translation included).
ZLB Behring Memo from Kanzy and Metzner to Vohwinkel, Schulte and Seemann re. Berinert P 10-fold concentrated (500U/mL) feasibility/stability dated Mar. 30, 2006.
Picture of HAEGARDA Packaging cited as Exhibit K28 in the Reply Brief filed by Shire Viropharma Incorporated on Jan. 30, 2018, against CSL Behring GmbH, in relation to European patent EP 2 968 434. (English translation included).
EU Summary of Products Characteristics Berinert 2000/3000; EU Package Leaflet re. Berinert 2000; EU Labels Berinert 2000; EU Package Leaflet Berinert 3000; EU Labels Berinert 3000 cited as Exhibit K29 in the Reply Brief filed by Shire Viropharma Incorporated on Jan. 30, 2018, against CSL Behring GmbH, in relation to European patent EP 2 968 434.
CSL Biotherapies information on Mix2Vial cited as Exhibit K30 in the Reply Brief filed by Shire Viropharma Incorporated on Jan. 30, 2018, against CSL Behring GmbH, in relation to European patent EP 2 968 434.
Legal opinion of Prof Leistner re. Sec. 3 para 4 German Patent Act cited as Exhibit K31 in the Reply Brief filed by Shire Viropharma Incorporated on Jan. 30, 2018, against CSL Behring GmbH, in relation to European patent EP 2 968 434. (English translation included).
BLA Approval letter CSL dated Jun. 22, 2017 cited as Exhibit K32 in the Reply Brief filed by Shire Viropharma Incorporated on Jan. 30, 2018, against CSL Behring GmbH, in relation to European patent EP 2 968 434.
MRFG Flow Chart of the Decentralised Procedure cited as Exhibit K33 in the Reply Brief filed by Shire Viropharma Incorporated on Jan. 30, 2018, against CSL Behring GmbH, in relation to European patent EP 2 968 434.
Head of Medicine Agency regarding Berinert 2000 cited as Exhibit K34 in the Reply Brief filed by Shire Viropharma Incorporated on Jan. 30, 2018, against CSL Behring GmbH, in relation to European patent EP 2 968 434.
Credit Suisse R&D Investor Briefing Dec. 5, 2017 cited as Exhibit K35 in the Reply Brief filed by Shire Viropharma Incorporated on Jan. 30, 2018, against CSL Behring GmbH, in relation to European patent EP 2 968 434.
CSL JP Morgan Conference Jan. 10, 2018 presentation cited as Exhibit K36 in the Reply Brief filed by Shire Viropharma Incorporated on Jan. 30, 2018, against CSL Behring GmbH, in relation to European patent EP 2 968 434.
Photographs of Presentation of the 22 Conference of the German Society for Agioedema cited as Exhibit K37 in the Reply Brief filed by Shire Viropharma Incorporated on Jan. 30, 2018, against CSL Behring GmbH, in relation to European patent EP 2 968 434. (English translation included).
ClinicalTrials.gov Glossary of Common Site Terms cited as Exhibit K40 in the Reply Brief filed by Shire Viropharma Incorporated on Jan. 30, 2018, against CSL Behring GmbH, in relation to European patent EP 2 968 434.
Clinical Development Success Rates 2006-2015 cited as Exhibit K42 in the Reply Brief filed by Shire Viropharma Incorporated on Jan. 30, 2018, against CSL Behring GmbH, in relation to European patent EP 2 968 434.
Exhibit to the Notification of the EPO dated Nov. 16, 2016 cited as Exhibit K43 in the Reply Brief filed by Shire Viropharma Incorporated on Jan. 30, 2018, against CSL Behring GmbH, in relation to European patent EP 2 968 434.
CSL Third Party Observation re. EP 14 762 434.4 cited as Exhibit K44 in the Reply Brief filed by Shire Viropharma Incorporated on Jan. 30, 2018, against CSL Behring GmbH, in relation to European patent EP 2 968 434.
Reply to Third Party Observation (Shire's reply) dated Mar. 2, 2017 cited as Exhibit K45 in the Reply Brief filed by Shire Viropharma Incorporated on Jan. 30, 2018, against CSL Behring GmbH, in relation to European patent EP 2 968 434.
Exhibit to the Notification of the EPO dated Apr. 28, 2017 cited as Exhibit K46 in the Reply Brief filed by Shire Viropharma Incorporated on Jan. 30, 2018, against CSL Behring GmbH, in relation to European patent EP 2 968 434.
EPO Intention to Grant dated May 19, 2017 cited as Exhibit K47 in the Reply Brief filed by Shire Viropharma Incorporated on Jan. 30, 2018, against CSL Behring GmbH, in relation to European patent EP 2 968 434.
Berinert SC Prophylaxis Meeting Minutes (Apr. 30, 2010) cited as Exhibit rop10 in the Reply Brief filed by CSL Behring GmbH on Apr. 3, 2018, against Shire Viropharma Incorporated in relation to European patent EP 2 968 434.
CSL Minutes Kick-off Meeting Berinert, volume-reduced (Jun. 25, 2010) cited as Exhibit rop11 in the Reply Brief filed by CSL Behring GmbH on Apr. 3, 2018, against Shire Viropharma Incorporated in relation to European patent EP 2 968 434.
Presentation Berinert Feasibility Study cited as Exhibit rop12 in the Reply Brief filed by CSL Behring GmbH on Apr. 3, 2018, against Shire Viropharma Incorporated in relation to European patent EP 2 968 434.
CSL Meeting Minutes PharmaPlan Committee Meeting Sep. 9-13, 2010 cited as Exhibit rop13 in the Reply Brief filed by CSL Behring GmbH on Apr. 3, 2018, against Shire Viropharma Incorporated in relation to European patent EP 2 968 434.
CSL 21st Project Review Committee Minutes Oct. 5, 2010 cited as Exhibit rop14 in the Reply Brief filed by CSL Behring GmbH on Apr. 3, 2018, against Shire Viropharma Incorporated in relation to European patent EP 2 968 434.
CSL Internal Target Product Profile cited as Exhibit rop15 in the Reply Brief filed by CSL Behring GmbH on Apr. 3, 2018, against Shire Viropharma Incorporated in relation to European patent EP 2 968 434.
CSL Monthly Project Report Berinert P/Sc Oct. 2010 and further reports cited as Exhibit rop16 in the Reply Brief filed by CSL Behring GmbH on Apr. 3, 2018, against Shire Viropharma Incorporated in relation to European patent EP 2 968 434.
CSL Minutes Berinert SC Project Team Kick-Off Meeting Dec. 1, 2010 and additional documents cited as Exhibit rop17 in the Reply Brief filed by CSL Behring GmbH on Apr. 3, 2018, against Shire Viropharma Incorporated in relation to European patent EP 2 968 434.
22nd Project Review Committee Meeting Feb. 10, 2011 and Minutes cited as Exhibit rop18 in the Reply Brief filed by CSL Behring GmbH on Apr. 3, 2018, against Shire Viropharma Incorporated in relation to European patent EP 2 968 434.
22nd Project Review Committee Meeting Feb. 10, 2011 Presentation cited as Exhibit rop19 in the Reply Brief filed by CSL Behring GmbH on Apr. 3, 2018, against Shire Viropharma Incorporated in relation to European patent EP 2 968 434.
23rd Project Review Committee Jun. 21 and 22, 2011 and final minutes and presenation cited as Exhibit rop20 in the Reply Brief filed by CSL Behring GmbH on Apr. 3, 2018, against Shire Viropharma Incorporated in relation to European patent EP 2 968 434.
24th Project Review Committee Oct. 7, 2011, presentation, 25th Project Review Committee Feb. 17, 2012, Research and Development Jul. 2, 2012 and R&D Sep. 11, 2012, R&D Feb. 11, 2013 cited (56) References Cited

OTHER PUBLICATIONS as Exhibit rop21 in the Reply Brief filed by CSL Behring GmbH on Apr. 3, 2018, against Shire Viropharma Incorporated in relation to European patent EP 2 968 434.
Center for Biologics and Research Application to FDA for Type B pre-IND Meeting cited as Exhibit rop22 in the Reply Brief filed by CSL Behring GmbH on Apr. 3, 2018, against Shire Viropharma Incorporated in relation to European patent EP 2 968 434.
ClinicalTrials.gov Archive NCT01760343 cited as Exhibit rop23 in the Reply Brief filed by CSL Behring GmbH on Apr. 3, 2018, against Shire Viropharma Incorporated in relation to European patent EP 2 968 434.
CSL Scientific Advise Meeting Oct. 13, 2011 re CSL830, Meeting Minutes cited as Exhibit rop24 in the Reply Brief filed by CSL Behring GmbH on Apr. 3, 2018, against Shire Viropharma Incorporated in relation to European patent EP 2 968 434.
Email Marco Cicardi Dec. 10, 2012 cited as Exhibit rop25 in the Reply Brief filed by CSL Behring GmbH on Apr. 3, 2018, against Shire Viropharma Incorporated in relation to European patent EP 2 968 434.
Email Thomas Craig Mar. 6, 2013, Summary and Follow up of CSL830 Steering Committee Meeting cited as Exhibit rop26 in the Reply Brief filed by CSL Behring GmbH on Apr. 3, 2018, against Shire Viropharma Incorporated in relation to European patent EP 2 968 434.
EMA Guideline for good clinical Practice cited as Exhibit rop28 in the Reply Brief filed by CSL Behring GmbH on Apr. 3, 2018, against Shire Viropharma Incorporated in relation to European patent EP 2 968 434.
Approval of Ethics Committee re. CSL830_2001 cited as Exhibit rop29 in the Reply Brief filed by CSL Behring GmbH on Apr. 3, 2018, against Shire Viropharma Incorporated in relation to European patent EP 2 968 434.
Press release ViroPharma dated Mar. 22, 2011 re AAAAI Meeting San Francisco cited as Exhibit rop30 in the Reply Brief filed by CSL Behring GmbH on Apr. 3, 2018, against Shire Viropharma Incorporated in relation to European patent EP 2 968 434.
ClinicalTrials.gov NCT00748202 cited as Exhibit rop31 in the Reply Brief filed by CSL Behring GmbH on Apr. 3, 2018, against Shire Viropharma Incorporated in relation to European patent EP 2 968 434.
Patient Information re. Berinert 2000 and 3000 cited in Triplik brief (Hoyng Rokh Monegier) date Apr. 30, 2018 (English translation included).
EMEA General Consideration for Clinical Trials cited in Triplik brief (Hoyng Rokh Monegier) date Apr. 30, 2018.
Notice from the EPO dated Jul. 5, 2017 re. Filing and Processing of TPOs under Art. 115 EPC cited in Triplik brief (Hoyng Rokh Monegier) date Apr. 30, 2018.
CSL Summary Basis for Regulatory Action Jun. 22, 2017 cited in Triplik brief (Hoyng Rokh Monegier) date Apr. 30, 2018.
Confirmatory Assignment and Owner's Rights Agreement cited in Triplik brief (Hoyng Rokh Monegier) date Apr. 30, 2018.
PCT Notifications under Rule 92bis.1 cited in Triplik brief (Hoyng Rokh Monegier) date Apr. 30, 2018.
Information brochure Federal Office for Drugs and Medical Products re. Clinical trials (non-commercial) cited in Quadruplik brief (rospatt osten press) dated Jun. 7, 2018 (English translation included).
CSL Certificate of IMP Release CSL830 1500 IU cited in Quadruplik brief (rospatt osten press) dated Jun. 7, 2018.
Excerpts of analyst reports 2012 cited in Quadruplik brief (rospatt osten press) dated Jun. 7, 2018.
Screenshot of the program of the project management CSL cited in Quadruplik brief (rospatt osten press) dated Jun. 7, 2018 (English translation included).
Excerpt CSL annual report 2010-2011 cited in Quadruplik brief (rospatt osten press) dated Jun. 7, 2018.
Trade register excerpt of ZLB Behring cited in Quadruplik brief (rospatt osten press) dated Jun. 7, 2018 (English translation included).
FDA Current Shortages cited in Quadruplik brief (rospatt osten press) dated Jun. 7, 2018.
Email Lisa Sjoberg (Shire) to Swedish Approval Authority dated Dec. 18, 2017 cited in Quadruplik brief (rospatt osten press) dated Jun. 7, 2018.
Cinryze 500 Unidades Polvy y Disolvente Para Solucion Inyectable cited in Quadruplik brief (rospatt osten press) dated Jun. 7, 2018 (English translation included).
EPO Boards of Appeal Decision T239/16 cited in Quadruplik brief (rospatt osten press) dated Jun. 7, 2018.
Patient Consent Form Novartis (re. Descision T239/16) cited in Quadruplik brief (rospatt osten press) dated Jun. 7, 2018.
Legal Opinion of Prof. Leistner re. Section 12 German Patent Act (Prior use Right) cited in Brief dated Jun. 22, 2018 (Hoyng Rokh Monegier) (English translation included).
EMA Update Shortage of Cinryze resolved Oct. 31, 2017 cited in Brief dated Jun. 22, 2018 (Hoyng Rokh Monegier).
CSL Drug Information to Healthcare Professionals Oct. 2, 2017 cited in Brief dated Jun. 22, 2018 (Hoyng Rokh Monegier).
EPA Case law regarding public availability cited in Brief dated Jun. 22, 2018 (Hoyng Rokh Monegier) (English translation included).
Email and draft Sanquin report cited in Brief dated Jun. 22, 2018 (Hoyng Rokh Monegier).
Sanquin report (final) May 15, 2009 cited in Brief dated Jun. 22, 2018 (Hoyng Rokh Monegier).
Daugherty et al. Formulations and delivery issues for monoclonal antibody therapeutics cited in Brief dated Jun. 22, 2018 (Hoyng Rokh Monegier).
Haller PharmTech.com Converting Intravenous Dosing to Subcutaneous Dosing with Recombinant Human Hyaluronidase cited in Brief dated Jun. 22, 2018 (Hoyng Rokh Monegier).
Kling Highly Concentrated Protein Formulations: Finding Solutions for the Next Generation of Parental Biologics cited in Brief dated Jun. 22, 2018 (Hoyng Rokh Monegier).
Sassin et al. Hypodermoclysis: An Alternative Infusion Technique cited in Brief dated Jun. 22, 2018 (Hoyng Rokh Monegier).
Shapiro Subcutaneous Immonoglobulin Therapy by Rapid Push is Preferred to Infusion by Pump: A Retrospective Analysis cited in Brief dated Jun. 22, 2018 (Hoyng Rokh Monegier).
Frost Recombinant human hyaluronidas (rHuPH20): an enabling platform for subutaneous drug and fluid administration cited in Brief dated Jun. 22, 2018 (Hoyng Rokh Monegier).
Contracts of the inventors and German translations of the highlighted parts cited in Brief dated Jun. 22, 2018 (Hoyng Rokh Monegier).
Label templates for CSL830_2001 with German comments cited in Brief dated Jun. 22, 2018 (Hoyng Rokh Monegier).
Email Dorothy Scott (FDA) re. Haegarda supply Sep. 1, 2017 cited in Brief dated Jun. 22, 2018 (Hoyng Rokh Monegier).
PRC Report R&D Dec. 11, 2012 cited in Brief dated Jun. 22, 2018 (Hoyng Rokh Monegier).
WIPO Section 325 of the administrative instructions under the PCT cited in Brief dated Jun. 22, 2018 (Hoyng Rokh Monegier).
Request for an extension of deadline (rospatt osten press) dated Jul. 31, 2017 (English translation included).
Statement of Defense (rospatt osten press) dated Oct. 27, 2017 (English translation included).
Brief dated Nov. 7, 2017 regarding process costs (Hoyng Rokh Monegier) (English translation included).
Brief dated Nov. 13, 2017 regarding submission of patent spec. (Hoyng Rokh Monegier) (English translation included).
Brief dated Nov. 13, 2017 regarding acknowledgement of paying security (Hoyng Rokh Monegier) (English translation included).
Brief dated Jan. 2, 2018 regarding security for proceedings (Hoyng Rokh Monegier) (English translation included).
Replik brief (Hoyng Rokh Monegier) dated Jan. 30, 2018 (English translation included).
Duplik brief (rospatt osten press) dated Apr. 3, 2018 (English translation included).
Brief submitting exhibit rop 32 in full dated Apr. 9, 2018 (English translation included).
Triplik brief (Hoyng Rokh Monegier) date Apr. 30, 2018 (English translation included).

(56) References Cited

OTHER PUBLICATIONS

Request for an extension of deadline (rospatt osten pross) dated May 25, 2018 (English translation included).
Brief regarding CSL's request extension of deadline (Hoyng Rokh Monegier) dated May 30, 2018 (English translation included).
Brief regarding CSL's request extension of deadline (rospatt osten pross) dated May 30, 2018 (English translation included).
Quadruplik brief (rospatt osten pross) dated Jun. 7, 2018 (English translation included).
Brief dated Jun. 22, 2018 (Hoyng Rokh Monegier) (English translation included).
Brief regarding impartiality of reporting judge (Hoyng Rokh Monegier) dated Jun. 29, 2018 (English translation included).
Brief dated Jul. 4, 2018 (rospatt osten pross) (English translation included).
Statement of Claim (Linklaters) dated Jun. 6, 2017 (English translation included).
Haller, Converting Intravenous Dosing to Subcutaneous Dosing with Recombinant Human Hyaluronidase, Pharmaceutical Technology, vol. 31(10).
Kling, Highly Concentrated Protein Formulations: Finding Solutions for the next Generation of Parenteral Biologics, BioProcess International, 12(5), 2014.
Ruconest® FDA Product Label.
Shire et al., Challenges in the Development of High Protein Concentration Formulations, Journal of Pharmaceutical Sciences, vol. 93(6), 2004.
Farkas et al., Z Gastroenterol. 1999, 37(6): 513-8.
Consent for Research ("Informed Consent") form (version date Jul. 9, 2012), for the enrollment of patients in Study No. CSL830_2001, which corresponds to ClinicalTrials.gov (National Institutes of Health) identification No. NCT01576523.
Notice of Service of Defendants' Initial Invalidity Contention, *Shire ViroPharma Incorporated* (Plaintiff) v. *CSL Behring LLC and CSL Behring GmbH* (Defendants), filed Apr. 3, 2018 in the United States District Court for the District of Delaware.
CSL Behring's Opening Claim Construction Brief, *Shire ViroPharma Incorporated* (Plaintiff) v. *CSL Behring LLC and CSL Behring GmbH* (Defendants), filed Jun. 18, 2018 in the United States District Court for the District of Delaware.
Declaration of Andrew MacGinnitie, M.D., Ph.D., Regarding Claim Construction, *Shire ViroPharma Incorporated* (Plaintiff) v. *CSL Behring LLC and CSL Behring GmbH* (Defendants), filed Jun. 18, 2018 in the United States District Court for the District of Delaware.
Plaintiff Shire ViroPharma Inc.'s Opening Claim Construction Brief, *Shire ViroPharma Incorporated* (Plaintiff) v. *CSL Behring LLC and CSL Behring GmbH* (Defendants), filed Jun. 25, 2018 in the United States District Court for the District of Delaware.
Minutes taken at the public hearing of the Landgericht München I, 7th Civil Division on Thursday, Dec. 7, 2018 (Jul. 12, 2018) in Munich, in the legal dispute Shire Viropharma Incorporated versus CSL Behring GmbH.

\* cited by examiner

SEQ ID NO: 1

```
  1 MASRLTLLTL LLLLLAGDRA SSNPNATSSS SQDPESLQDR GEGKVAPTVI SKMLFVEPIL
 61 EVSSLPTTMS TTNSATKITA NTTDEPTTQP TTEPTTQPTI QPTQPTTQLP TDSPTQPTTG
121 SFCPCPVTLC SDLESHSTEA VLGDALVDPS LKLYHAPSAM KKVETNMAFS PFSIASLLTQ
181 VLLGAGENTK TNLESILSYP KDFTCVHQAL KGPTTKGVTS VSQIPHSPDL AIRDTFVNAS
241 RTLYSSSPRV LSMNSDANLE LINTWVAKNT NNKISRLLDS LPSDTRLVLL NAIYLSAKWK
301 TTFDPKKTRM EPFHFKNSVI KVPMMNSKRY PVAHPIDQTL KAKVGQLQLS HNLSLVILVP
361 QNLKHRLEDM EQALSPSVFK AIMEKLEMSK PQPTLLTLPR IKVTTSQDML SIMEKLEFPD
421 FSYDLNLCGL TEDPDLQVSA MQHQTVLELT ETGVEAAAAS AISVARTLLV FEVQQPFLFV
481 LWDQQHKFPV FMGRVYDPRA
```

C1-INH COMPOSITIONS AND METHODS FOR THE PREVENTION AND TREATMENT OF DISORDERS ASSOCIATED WITH C1 ESTERASE INHIBITOR DEFICIENCY

CROSS REFERENCE TO RELATED APPLICATIONS

This application is a continuous application of U.S. patent application Ser. No. 15/411,744, filed on Jan. 20, 2017, which is a continuation application of U.S. patent application Ser. No. 14/855,168, filed on Sep. 15, 2015, now U.S. Pat. No. 9,616,111, which is a continuation of International Patent Application No. PCT/US14/30309, filed Mar. 1, 2014 which claims priority under 35 U.S.C. § 119(e) to U.S. Provisional Patent Application No. 61/791,399, filed Mar. 15, 2013. The foregoing application is incorporated by reference herein.

INCORPORATION-BY-REFERENCE-OF-SEQUENCE LISTING

The contents of the file named "SHR-1204US_ST25.txt", which was created on Jan. 20, 2017 and is 5 KB in size, are hereby incorporated by reference in their entirety.

FIELD OF THE INVENTION

The present invention relates to the field of therapeutic agents and methods of use thereof. Specifically, the instant invention provides compositions and methods for the treatment and/or prevention of disorders associated with C1 esterase inhibitor deficiency.

BACKGROUND OF THE INVENTION

Several publications and patent documents are cited throughout the specification in order to describe the state of the art to which this invention pertains. Full citations of these references can be found throughout the specification. Each of these citations is incorporated herein by reference as though set forth in full.

Hereditary angioedema (HAE) is a rare, life-threatening, genetic disorder caused by a deficiency of the C1esterase inhibitor (see generally www.haei.org and www.haea.org). At least 6,500 people in the United States and at least 10,000 people in Europe have HAE. HAE patients experience recurrent, unpredictable, debilitating, life-threatening attacks of inflammation and submucosal/subcutaneous swelling. The inflammation is typically of the larynx, abdomen, face, extremities, and urogenital tract. This genetic disorder is a result of a defect in the gene controlling the synthesis of the C1 esterase inhibitor. Accordingly, restoring the levels of active C1 esterase inhibitor in these patients to or near normal levels is an effective measure for treating HAE. Still, new and improved methods of treating and preventing disorders associated with a deficiency of the C1esterase inhibitor, such as HAE, are desired.

SUMMARY OF THE INVENTION

In accordance with the instant invention, methods for inhibiting, treating, and/or preventing a disorder associated with a deficiency in C1 esterase inhibitor in a subject are provided. In a particular embodiment, the method comprises administering a composition comprising at least one. C1 esterase inhibitor.

In accordance with the instant invention, therapeutic compositions are also provided. In a particular embodiment, the composition comprises at least one C1 esterase inhibitor and, optionally, at least one pharmaceutically acceptable carrier for delivery (e.g. intravenous or subcutaneous delivery). Kits comprising a composition comprising at least one C1 esterase inhibitor are also provided herein.

DETAILED DESCRIPTION OF THE INVENTION

The restoration of active C1 esterase inhibitor levels in patients having a disorder associated with deficient or reduced levels of active C1 esterase inhibitor (e.g., HAE) is an effective measure for treating such disorders. Currently, C1 esterase inhibitor (such as Cinryze® (ViroPharma, Inc.; Exton, Pa.)) is administered to a patient intravenously by a medical professional. Herein, formulations of a C1 esterase inhibitor (such as Cinryze®) are provided which are also effective for subcutaneous (SC) administration. Surprisingly, the subcutaneous administration of the C1 esterase inhibitor is sufficient to maintain the blood levels of the C1 esterase inhibitor. The SC administration of a C1 esterase inhibitor fulfills an unmet medical need due to the limitations of intravenous administration in HAE patients.

In accordance with the instant invention, compositions and methods for inhibiting (e.g., reducing or slowing), treating, and/or preventing a disorder associated with C1 esterase inhibitor deficiency in a subject are provided. In a particular embodiment, the methods comprise administering (e.g., subcutaneously or intravenously) to a subject in need thereof at least one C1 esterase inhibitor. In a particular embodiment, the C1 esterase inhibitor is administered subcutaneously after an initial administration of the C1 esterase inhibitor intravenously.

Figure 1:
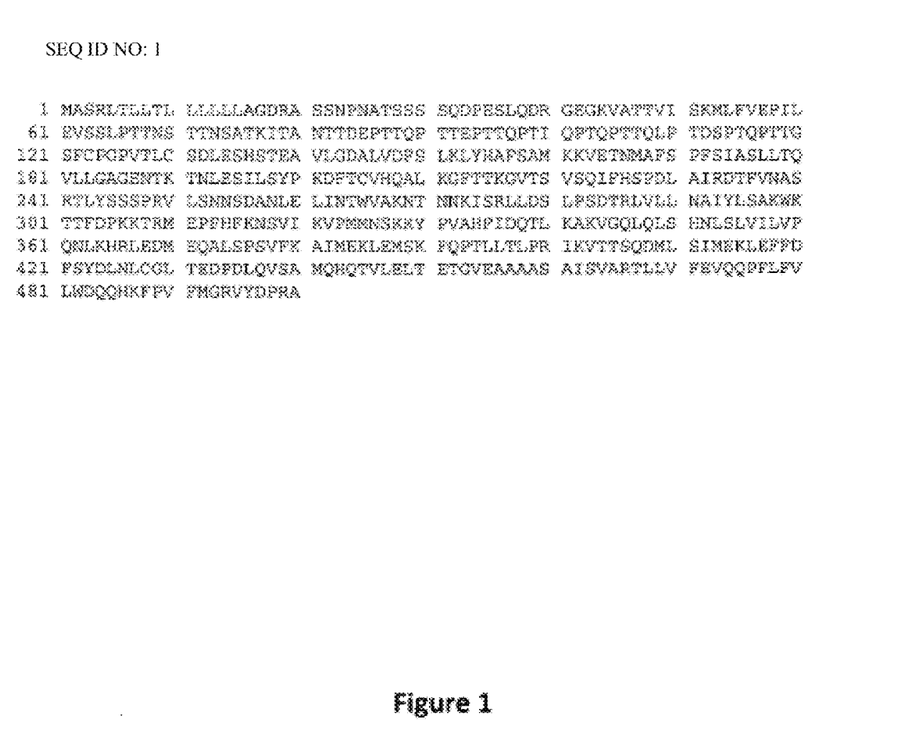
FIG. 1 provides an amino acid sequence of human C1 esterase inhibitor.

C1 esterase inhibitors are also known as C1 inhibitors (C1 INH). C1 esterase inhibitors are inhibitors of complement C1 and belong to the superfamily of serine proteinase inhibitors. Human C1 esterase inhibitor is a protein of 500 amino acids, including a 22 amino acid signal sequence (Carter et al, (1988) Eur. J. Biochem., 173:163). In plasma, the C1 esterase inhibitor is a heavily glycosylated glycoprotein of approximately 76 kDa (Perkins et al. (1990) J. Mol. Biol., 214:751). The activity of a C1 esterase inhibitor may be assayed by known methods (see, e.g., Drouet et al. (1988) Clin. Chim. Acta., 174:121.30). In a particular embodiment, the C1 esterase inhibitor is human. An amino acid sequence of human C1 esterase inhibitor is provided in GenBank Accession No. CAA30314 (see also GeneID: 710, which also provides nucleotide sequences of the C1 esterase inhibitor) and FIG. 1. A C1 esterase inhibitor for use in the methods of the instant invention may have an amino acid sequence that has at least 65, 70, 75, 80, 85, 90, 95, 98, 99, or 100% identity with the amino acid sequence of FIG. 1. The C1 esterase inhibitor may be isolated or purified from plasma (e.g., human plasma) or recombinantly produced. When purified from plasma, the C1 esterase inhibitor may be nanofiltered and pasteurized. In a particular embodiment, the plasma-derived C1 esterase inhibitor is Cinryze®. In a particular embodiment, the C1 esterase inhibitor is present in the compositions of the instant invention at high concentration. Indeed, compositions comprising very high levels of C1 esterase inhibitor have been determined to be surprisingly stable and active. In a particular embodiment, the C1 esterase inhibitor is present at about 250 U/ml to about 1000 U/ml, about 400 U/ml to about 600 U/ml, or about 500 U/ml.

In a particular embodiment, the compositions of the instant invention do not contain citrate or citric acid. The compositions lacking citrate and citric acid are particularly useful for the subcutaneous administration of the C1 esterase inhibitor as citrate/citric acid can cause an injection site reaction. In a particular embodiment, the buffer of the instant compositions is sodium phosphate (e.g., about 5 mM to about 50 mM sodium phosphate, about 10 mM to about 30 mM sodium phosphate, or about 20 mM sodium phosphate). In a particular embodiment (e.g., for intravenous administration), the buffer of the instant compositions comprises a carboxylic group. For example, the buffer may be, without limitation, citrate, succinate, tartarate, maleate, acetate, and salts thereof. In a particular embodiment, the buffer of the instant composition is citrate or sodium citrate (e.g., about 5 mM to about 50 mM sodium citrate, about 10 mM to about 30 mM sodium citrate, or about 20 mM sodium citrate).

The compositions of the instant invention may have a pH range of about 6.5 or higher, particularly about 6.5 to about 8.0, particularly about 6.5 to about 7.5, and more particularly about 6.5 to about 7.0.

The compositions of the instant invention may also comprise polysorbate 80 (TWEEN). Compositions comprising polysorbate 80 are particularly useful as they reduce/mitigate, protein aggregation. Polysorbate 80 can also limit protein interactions when the composition comes into contact with silicon containing lubricants/oils such as those used in syringes and other administration devices.

Compositions comprising polysorbate 80 are also useful for lyophilized preparations. In a particular embodiment, the polysorbate 80 is present at a concentration of about 0.01% to about 0.1%, particularly about 0.025% to about 0.075%, particularly about 0.05%.

The compositions of the instant invention may also comprise sucrose. Sucrose can be added as a "bulking" agent as well as a lyo-protectant. In a particular embodiment, sucrose is added to compositions to be lyophilized. In a particular embodiment, the compositions comprise about 25 mM to about 125 mM sucrose, particularly about 50 mM to about 100 mM sucrose.

The compositions of the instant invention may also comprise at least one amino acid or salt thereof, particularly methionine and/or arginine. Arginine carries a positive charge on its side chain can be used to buffer solutions with phosphate. Methionine acts as a stabilizer (e.g., by limiting oxidation). The amino acids may be present in the composition as individual amino acids or present as short peptides (e.g., 2 to about 5 amino acids, particularly di-peptides or tri-peptides).

As stated hereinabove, the instant invention encompasses methods of treating, inhibiting, and or preventing any condition or disease associated with an absolute or relative deficiency of functional C1 esterase inhibitor. Such disorders include, without limitation, acquired angioedema (AAE) and hereditary angioedema (HAE). In a particular embodiment, the disorder is HAE and/or the attacks associated therewith. As stated hereinabove, HAE is a life-threatening and debilitating disease that manifests as recurrent, submucosal/subcutaneous swelling attacks due to a deficiency of C1 esterase inhibitor (Zuraw, B. L. (2008) N. Engl. J. Med., 359:1027-1036). In a particular embodiment, the hereditary angioedema is type I or type II. Both type I and type II have a defective gene for the synthesis of C1 esterase inhibitor that produce either no C1 inhibitor (HAE type I) or a dysfunctional C1 inhibitor (HAE type II) (Rosen et al. (1965) Science 148: 957-958; Bissler et al. (1997) Proc. Assoc. Am. Physicians 109: 164-473; Zuraw et al. (2000) J. Allergy Clin. Immunol. 105: 541-546; Bowen et al. (2001) Clin. Immunol. 98: 157-163).

The methods of the instant invention encompass the administration of at least one C1 esterase inhibitor. Compositions comprising at least one C1 esterase inhibitor and, optionally, at least one pharmaceutically acceptable carrier (e.g., one suitable for subcutaneous or intravenous administration) are encompassed by the instant invention. Such compositions may be administered, in a therapeutically effective amount, to a patient in need thereof for the treatment of a disorder associated with C1 esterase inhibitor deficiency. The instant invention also encompasses kits comprising at least one composition of the instant invention, e.g., a composition comprising at least one C1 esterase inhibitor and, optionally, at least one pharmaceutically acceptable carrier (e.g., one suitable for intravenous or subcutaneous administration). The kits may further comprise at least one of reconstitution buffer(s), syringes (e.g., disposable) for parenteral (e.g., subcutaneous) injection, and instruction material. In a particular embodiment, the kit comprises at least one pre-loaded syringe comprising the C1 esterase inhibitor and at least one pharmaceutically acceptable carrier. For example, a syringe may be loaded with at least one C1 esterase inhibitor with at least one pharmaceutically acceptable carrier for administration (e.g., intravenous or subcutaneous administration). Alternatively, a single syringe may be loaded with lyophilized C1 esterase inhibitor. In a particular embodiment, the preloaded syringes have a pharmaceutical composition that contains polysorbate 80 as a component (e.g., in an amount that prevents protein-silicone interaction or protein aggregation).

The agents and compositions of the present invention can be administered by any suitable route, for example, by injection (e.g., for local (direct) or systemic administration. In a particular embodiment, the composition is administered subcutaneously or intravenously. In general, the pharmaceutically acceptable carrier of the composition is selected from the group of diluents, preservatives, solubilizers, emulsifiers, adjuvants and/or carriers. The compositions can include diluents of various buffer content (e.g., Tris HCl, acetate, phosphate), pH and ionic strength; and additives such as detergents and solubilizing agents (e.g., Tween 80, Polysorbate 80), antioxidants (e.g., ascorbic acid, sodium metabisulfite), preservatives (e.g., Thimersol, benzyl alcohol) and bulking substances (e.g., lactose, mannitol). The pharmaceutical composition of the present invention can be prepared, for example, in liquid form, or can be in dried powder form (e.g., lyophilized for later reconstitution).

In a particular embodiment, the compositions are formulated in lyophilized form. Where the compositions are provided in lyophilized form, the compositions are reconstituted prior to use (e.g., within an hour, hours, or day or more of use) by an appropriate buffer (e.g., sterile water, a sterile saline solution, or a sterile solution comprising the appropriate pharmaceutically acceptable carriers (e.g., to reconstitute the compositions as described hereinabove). The reconstitution buffer(s) may be provided in the kits of the instant invention or may be obtained or provided separately.

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Selection of a suitable pharmaceutical preparation depends upon the method of administration chosen. In this instance, a pharmaceutical preparation comprises the molecules dispersed in a medium that is compatible with the tissue to which it is being administered. Methods for preparing parenterally or subcutaneously administrable compositions are well known in the art (see, e.g., Remington's Pharmaceutical Science (E.W. Martin, Mack Publishing Co., Easton, Pa.)).

As stated hereinabove, agents of the instant invention are administered parenterally—for example by intravenous injection into the blood stream and/or by subcutaneous injection. Pharmaceutical preparations for parenteral, intravenous, and subcutaneous injection are known in the art. If parenteral injection is selected as a method for administering the molecules, steps should be taken to ensure that sufficient amounts of the molecules reach their target cells to exert a biological effect.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., parenterally or subcutaneous. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Dosage units may be proportionately increased or decreased based on the weight of the patient. Appropriate concentrations for alleviation of a particular pathological condition may be determined by dosage concentration curve calculations. Appropriate dosage unit may also be determined by assessing the efficacy of the treatment.

The pharmaceutical preparation comprising the molecules of the instant invention may be administered at appropriate intervals, for example, daily, every other day, every three days, five out of every 7 days, or at least one, two or three times a week or more until the pathological symptoms are reduced or alleviated, after which the dosage may be reduced to a maintenance level. The appropriate interval in a particular case would normally depend on the condition of the patient.

In a particular embodiment, the C1 esterase inhibitor is present in the composition or is administered in the range of about 100 Units to about 10,000 Units; about 500 Units to about 5,000 Units; about 1,000 Units to about 3,500 Units, or about 1,500 Units to about 2,500 Units. In a particular embodiment, at least about 2,000 Units is used. In a particular embodiment, a high initial dose of the C1 esterase inhibitor (as listed above (may be administered intravenously)) is used, followed by lower maintenance doses. For example, the high initial dose may be at least 1.5, 2, 3, 4, or 5 times the subsequent doses. In a particular embodiment, the C1 esterase inhibitor is present in the maintenance composition or is administered far maintenance in the range of about 100 Units to about 5,000 Units; about 250 Units to about 2,000 Units; about 250 Units to about 1,000 Units; or about 500 Units. The high initial does of the C1 esterase inhibitor is optional in the methods of the instantly claimed invention (e.g., may be optional with prophylactic methods).

In a particular embodiment, the C1 esterase inhibitor is administered with a frequency and dosage so as to increase the C1 esterase inhibitor level to at least about 0.3 or, more particularly, 0.4 U/ml or more up to about 1 U/ml (1 Unit/ml is the mean quantity of C1 inhibitor present in 1 ml of normal human plasma) in the blood of the subject. For example, the C1 esterase inhibitor level may be kept at or above 0.4 U/ml for at least 50%, at least 75%, at least 90%, at least 95% or more of time or all of the time (e.g., the time during which drug is being administered). For example, the administration of a 2000 U initial dose of C1 esterase inhibitor followed by 250 U everyday or 500 U every other day results in the maintenance of just below 0.4 U/ml in blood. Further, the administration of a 2000 U initial dose of C1 esterase inhibitor followed by 1000 U every 3 days results in the maintenance of about 0.4 U/ml in blood. Notably, for ease of use by the patient, less frequent administrations may be preferred. The administration of a 2000 U initial dose of C1 esterase inhibitor followed by 500 U everyday with weekend holidays from administration (i.e., 5 out of 7 days) also results in the maintenance of about 0.4 U/ml or higher in blood. Notably, the administration of only the maintenance doses leads to increased and physiologically relevant blood levels of the C1 esterase inhibitor, but delayed compared to those receiving an initial high dose.

Definitions

The singular forms "a," "an," and "the" include plural referents unless the context clearly dictates otherwise.

As used herein, the term "about" may refer to ±5%, ±2%, or ±1%.

As used herein, the terms "host," "subject," and "patient" refer to any animal, including humans.

As used herein, the term "prevent" refers to the prophylactic treatment of a subject who is at risk of developing a condition (e.g., HAE or HAE attack) resulting in a decrease in the probability that the subject will develop the condition.

The term "treat" as used herein refers to any type of treatment that imparts a benefit to a patient afflicted with a disorder, including improvement in the condition of the patient (e.g., in one or more symptoms), delay in the progression of the condition, etc. In a particular embodiment, the treatment of HAE results in at least a reduction in the severity and/or number of HAE attacks.

The phrase "effective amount" refers to that amount of therapeutic agent that results in an improvement in the patient's condition. A "therapeutically effective amount" of a compound or a pharmaceutical composition refers to an amount effective to prevent, inhibit, treat, or lessen the symptoms of a particular disorder or disease.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., TWEEN 80, Polysorbate 80), emulsifier, buffer (e.g., Tris acetate, phosphate), water, aqueous solutions, oils, bulking substance (e.g., lactose, mannitol), cryo-/lyo-protectants, tonicity modifier, excipient, auxiliary agent or vehicle with which an active agent of the present invention is administered. Suitable pharmaceutical carriers are described in "Remington's Pharmaceutical Sciences" by E.W. Martin (Mack Publishing Co., Easton, Pa.); German), A. R., Remington: The Science and Practice of Pharmacy, (Lippincott, Williams and Wilkins); Liberman, et al., Eds., Pharmaceutical Dosage Forms, Marcel Decker, New York, N.Y.; and Kibbe, et al., Eds., Handbook of Pharmaceutical Excipients, American Pharmaceutical Association, Washington.

The term "isolated" may refer to protein, nucleic acid, compound, or cell that has been sufficiently separated from the environment with which it would naturally be associated (e.g., so as to exist in "substantially pure" form). "Isolated" does not necessarily mean the exclusion of artificial or synthetic mixtures with other compounds or materials, or the presence of impurities that do not interfere with the fundamental activity, and that may be present, for example, due to incomplete purification.

The term "substantially pure" refers to a preparation comprising at least 50-60% by weight of a given material (e.g., nucleic acid, oligonucleotide, protein, etc.). In certain embodiments, the preparation comprises at least 75% by weight, particularly 90-95% or more by weight of the given compound. Purity is measured by methods appropriate for the given compound (e.g. chromatographic methods, agarose or polyacrylamide gel electrophoresis, HPLC analysis, and the like).

The following example is provided to illustrate various embodiments of the present invention. The example is illustrative and is not intended to limit the invention in any way.

EXAMPLE

Spin Concentration Studies

The protein was loaded into the spin concentrators and rotated at 10,500 rpms for 5 to 10 minutes. When the samples stopped rotating, the final volumes in the spin concentrators were recorded and a rough protein concentration was calculated for each one. Additional protein was added to the spin concentrators and rotated until the desired protein concentration was reached, at which point a UV measurement was made. At each target protein concentration a UV and viscosity measurement was performed. The above procedure continued until the viscosity of the protein prevented the sample from being further concentrated.

Viscosity Measurements

Viscosity was determined by measuring the amount of time the sample took to be drawn to a predetermined distance in a gel loading pipette tip. In order to calculate the sample viscosity, a standard curve was first prepared using a set of standards with known viscosities. Sucrose (or Brix) solutions are suitable for preparing such a curve, but any material with known viscosity at a defined temperature should be appropriate.

In order to make a measurement, the pipette plunger is depressed, the pipette tip is inserted into the sample vial, the plunger is released, and the time for the fluid to travel a predetermined distance in the pipette tip was measured with a stop watch. The distance used for these experiments was 30 µL of water. In important note, a pipette tip is only reliable for a single measurement, so multiple tips are used to make replicate measurements of a sample. Also, the volume to be drawn into the pipette tip should be larger than the volume marked on the tip to ensure a uniform pull on the sample during a measurement. For a 30 µL volume mark on the pipette tip, the micropipette was set to draw 42 µL.

Results

Figure 2:
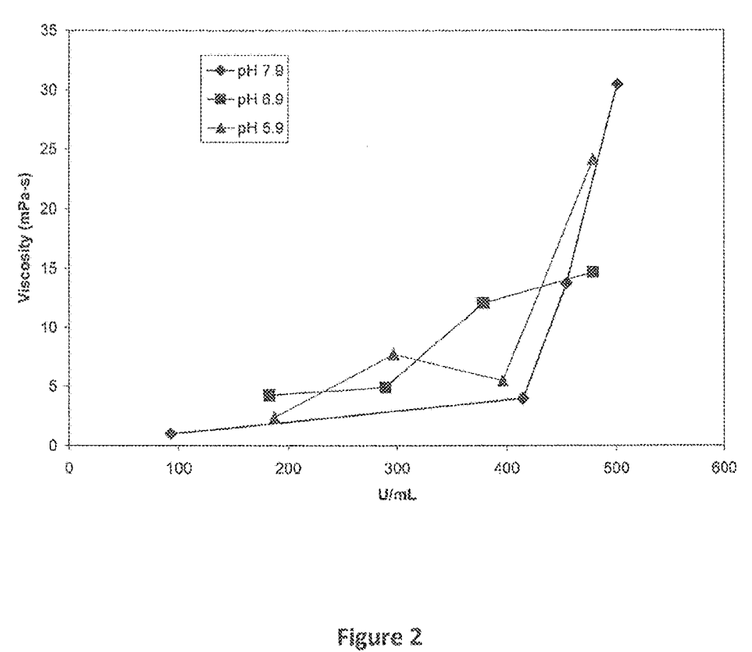
FIG. 2 provides a graph of the effect of protein concentration on viscosity for initial spin concentration samples.

The instant example determined the ability to develop a higher concentration liquid formulation of C1 INH as a monoformulation. The initial studies focused on concentration of the stock solution of C1 INH using a spin concentration method. The solutions were initially adjusted for pH but no other excipient was added. Three pH values were investigated (pH 5.9, 6.9, and 7.9). Upon spin concentration, all of the solutions remained clear up to concentrations up ~500 U/ml (approximately 100 nag/ml) for all pH values tested (Table 1). While the solubility limit was not reached in these studies, there were measurable increases in viscosity as the concentrations exceeded 300 U/ml (FIG. 2). At all pH values, the viscosity begins to increase markedly when the C1 INH concentration goes above 400 U/ml.

TABLE 1

Final concentrations (in U/mL) and viscosities for samples prepared during the spin concentration experiments. These values were based on the initial 160 U/mL concentration of the initial bulk drug.

| 7.9 U/mL | viscosity | 6.9 U/mL | viscosity | 5.9 U/mL | viscosity |
| --- | --- | --- | --- | --- | --- |
| 93.12 | 0.99 | 182.4 | 4.23 | 187.2 | 2.36 |
| 415.18 | 3.95 | 289.4 | 4.90 | 296.9 | 7.71 |
| 454.81 | 13.74 | 378.6 | 12.08 | 396.7 | 5.46 |
| 501.17 | 30.43 | 479.0 | 14.67 | 478.8 | 24.09 |

A larger feasibility study was performed examining different buffers (20 mM phosphate, 20 mM citrate, and 20 mM Tris) at each of the three target values. Samples of both 400 U/ml and 500 U/ml were prepared and evaluated for stability after one week at 40° C. and after two weeks at 25° C. The initial viscosity levels were well above the values for pure water (~1 mPa-s), but well within the limits usually set for use as an injectable product (Table 2). The viscosity values for the 400 U/ml samples were less than at 500 U/ml, usually by 7 to 1.0 mPa-s. Upon storage at 40° C. for one week, the viscosity of all of the samples increased. At pH 5.9, all of the same gelled, likely due to thermally induced aggregation. For the remaining formulations, the viscosity increased to some degree. In some cases these values exceeded 30 mPa-s. The increase in viscosity was less upon 25° C. storage than at 40° C. There was little, if any, change, for the samples at pH 6.9, indicating that pH 6.9 may be more favorable for long-term storage stability.

TABLE 2

Viscosity at t0 and after one week of storage at 40° C. (t1). Viscosity is reported in mPa-s.

| pH | [C1 INH] | Buffer | t0 | t1 | t2 |
| --- | --- | --- | --- | --- | --- |
| 5.9 | 400 | phosphate | 13.3 ± 0.6 | gel | 17.4 ± 2.1 |
|  | 500 |  | 24.6 ± 1.5 | gel | 36.9 ± 7.3 |
|  | 400 | histidine | 14.7 ± 0.8 | gel | 19.1 ± 2.5 |
|  | 500 |  | 27.7 ± 3.8 | gel | 27.7 ± 3.8 |
| 6.9 | 400 | phosphate | 12.2 ± 1.5 | 16.1 ± 0.6 | 11.9 ± 3.0 |
|  | 500 |  | 20.8 ± 2.0 | 35.3 ± 2.1 | 32.1 ± 7.7 |
|  | 400 | citrate | 7.4 ± 0.8 | 9.2 ± 0.7 | 7.1 ± 0.6 |
|  | 500 |  | 14.4 ± 3.2 | 19.8 ± 1.1 | 12.6 ± 0.5 |

TABLE 2-continued

Viscosity at t0 and after one week of storage at 40° C. (t1).
Viscosity is reported in mPa-s.

| pH  | [C1 INH] | Buffer    | t0         | t1         | t2         |
|-----|----------|-----------|------------|------------|------------|
| 7.9 | 400      | phosphate | 8.2 ± 1.2  | 12.8 ± 0.7 | 22.0 ± 3.5 |
|     | 500      |           | 16.2 ± 1.4 | 23.1 ± 2.1 | 25.5 ± 7.5 |
|     | 400      | tris      | 14.1 ± 0.7 | 18.7 ± 0.7 | 30.0 ± 3.8 |
|     | 500      |           | 20.5 ± 0.9 | 33.3 ± 6.2 | 31.0 ± 1.8 |

Notably, at pH 6.9, citrate formulations had lower viscosity values than for phosphate, while at pH 7.9, phosphate buffer produced lower viscosities than his buffer. Higher viscosities will mean greater force will be required to deliver a specified volume of the drug within a certain time frame.

The purity by RP HPLC was initially near 86 to 87% for the formulations at pH 6.9 and above (Table 3). The initial levels were lower at pH 5.9, suggesting that some degradation had already occurred just in the process of preparing the samples. Upon storage for one week at 40° C., the pH 5.9 samples gelled, making analysis by RP HPLC impossible. For all of the other samples, the percent purity was essentially unchanged, indicating that little, if any, chemical degradation occurs for storage under these conditions.

TABLE 3

Percent purity by RP HPLC upon storage at 25° C. (t2) or 40° C. (t1)

| pH  | [C1 INH] | Buffer    | t0          | t1          | t2          |
|-----|----------|-----------|-------------|-------------|-------------|
| 5.9 | 400      | phosphate | 82.87 ± 0.75| gel         | 81.10 ± 2.11|
|     | 500      |           | 84.74 ± 1.24| gel         | 83.61 ± 1.02|
|     | 400      | histidine | 84.11 ± 1.53| gel         | 85.34 ± 1.55|
|     | 500      |           | 86.36 ± 0.76| gel         | 82.99 ± 0.64|
| 6.9 | 400      | phosphate | 87.14 ± 0.67| 88.59 ± 0.29| 85.19 ± 2.00|
|     | 500      |           | 86.44 ± 1.49| 85.65 ± 1.32| 84.07 ± 1.24|
|     | 400      | citrate   | 86.67 ± 1.36| 82.92 ± 1.48| 86.03 ± 0.87|
|     | 500      |           | 86.89 ± 1.24| 86.74 ± 0.88| 84.42 ± 1.19|
| 7.9 | 400      | phosphate | 86.09 ± 1.14| 85.29 ± 0.84| 85.98 ± 0.90|
|     | 500      |           | 86.47 ± 1.15| 83.57 ± 1.33| 84.00 ± 0.97|
|     | 400      | tris      | 87.14 ± 0.98| 81.74 ± 7.89| 86.14 ± 0.81|
|     | 500      |           | 88.74 ± 0.82| 87.24 ± 1.47| 87.30 ± 0.95|

For samples stored for two weeks at 25° C., there were small losses, comparable to what was seen at t1. Together, the RP HPLC data indicate that there are small losses due to chemical degradation. Higher pH seems to diminish the rate of degradation and there may be some sensitivity to buffer composition.

While the chemical stability of C1 TNH seems to be unchanged upon storage, there is come physical instability observed as indicated by SEC (Table 4). There are other proteins present in the C1 INH mixture, leading to an overall 'purity' of about ~67% at t0. Upon storage at 40° C. for one week (t1), the overall monomer content of the samples decreased to 54-56% for the samples with pH 6.9 and higher. There was little difference between the two different pH conditions, the different buffers and the two protein concentrations. When stored for two weeks at 25° C. (t2), the pH 5.9 samples did not gel, as they did at the higher storage temperature. However, there was appreciably higher degradation, especially with histidine buffer. For these at pH 6.9 or 7.9, the loss as measured by SEC was about 2% or so, compared to the 10-12% loss at the higher temperature for half of the time.

TABLE 4

Monomer content by SEC upon storage at 25° C. (t2) or 40° C. (t1).

| PH  | [C1 INH] | Buffer    | t0          | t1          | t2          |
|-----|----------|-----------|-------------|-------------|-------------|
| 5.9 | 400      | phosphate | 68.32 ± 1.04| gel         | 62.56 ± 0.94|
|     | 500      |           | 67.19 ± 0.14| gel         | 61.46 ± 0.14|
|     | 400      | histidine | 64.68 ± 0.42| gel         | 46.58 ± 1.09|
|     | 500      |           | 66.60 ± 0.08| gel         | 44.48 ± 1.04|
| 6.9 | 400      | phosphate | 67.85 ± 0.22| 55.29 ± 0.36|             |
|     | 500      |           | 67.41 ± 0.36| 54.79 ± 0.14| 65.45 ± 0.23|
|     | 400      | citrate   | 67.82 ± 0.07| 56.14 ± 0.41| 65.49 ± 0.16|
|     | 500      |           | 67.43 ± 0.30| 56.59 ± 0.33| 65.03 ± 0.36|
| 7.9 | 400      | phosphate | 67.85 ± 0.09| 54.96 ± 0.52| 61.31 ± 0.25|
|     | 500      |           | 67.58 ± 0.40| 55.57 ± 0.56| 64.98 ± 0.50|
|     | 400      | tris      | 67.63 ± 0.27| 55.40 ± 0.30| 65.70 ± 0.56|
|     | 500      |           | 67.67 ± 0.47| 56.18 ± 0.64| 66.19 ± 0.84|

The data indicate that the rate of degradation will be about 13-fold to 35-fold slower at 4° C. than at 25° C. The higher estimate comes from using an Arrhenius plot. The lower estimate comes from determine the average loss as the temperature is decreased by 5° C. and extrapolating to a storage temperature of 40° C. Using the current data as an indicator, this predicts a loss of about 3 to 10% loss after two years at refrigerated temperatures. In other words, a liquid formulation appears to be quite stable based on these data. Furthermore, the degradation rates are roughly comparable between the 400 U/mL and 500 U/ml samples, suggesting that developing the higher concentration formulation is just as viable.

The degradation rate is much faster at pH 5.9, leading to gelation at 40° C. and greater losses at 25° C., Thus, further pH/buffer screening will focus on the pH 6.5 to 8.0 range. There is a clear buffer effect on viscosity and possibly also on stability.

The studies demonstrated that there is not a solubility limit to preparing C1 INH at concentrations up to 500 U/ml. There is an increase in viscosity once the concentrations reach the 400-500 U/ml range (which is buffer dependent with citrate being better than phosphate which is better than Tris), but they are manageable and still allow facile delivery by injection for standard syringe systems. In general, C1 INH is relatively stable to chemical degradation, as determined by RP HPLC.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A pharmaceutical composition comprising C1 esterase inhibitor, sodium citrate, and having a pH ranging from 6.5-8.0, wherein the C1 esterase inhibitor has a concentration of about 500 U/mL, and wherein the C1 esterase inhibitor comprises the amino acid sequence of residues 23 to 500 of SEQ ID NO: 1.

2. The pharmaceutical composition of claim 1, wherein the pH is between about 6.5 to about 7.5.

3. The pharmaceutical composition of claim 1, wherein the pH is between about 6.5 to about 7.0.

4. The pharmaceutical composition of claim 1, wherein the sodium citrate is present at about 10 mM to about 30 mM.

5. The pharmaceutical composition of claim 1, wherein the sodium citrate is present at 10 mM to 30 mM.

6. The pharmaceutical composition of claim 1, wherein the sodium citrate is present at about 10 mM.

7. The pharmaceutical composition of claim 1, wherein the composition further comprises at least one amino acid or salt thereof.

8. The pharmaceutical composition of claim 1, wherein the C1 esterase inhibitor is present in the composition in the range of about 1500 U to about 2500 U.

9. The pharmaceutical composition of claim 1, wherein the C1 esterase inhibitor is present in the composition in at least about 2000 U.

10. The pharmaceutical composition of claim 1, wherein the C1 esterase inhibitor is present in the composition at about 2000 U.

11. The pharmaceutical composition of claim 9, wherein the C1 esterase inhibitor is present in the composition less than about 5000 U.

12. The pharmaceutical composition of claim 1, wherein the C1 esterase inhibitor is present in the composition in about 5000 U.

13. The pharmaceutical composition of claim 1, wherein the C1 esterase inhibitor is isolated or purified from human plasma.

14. The pharmaceutical composition of claim 13, wherein the C1 esterase inhibitor isolated or purified from human plasma is nanofiltered.

15. The pharmaceutical composition of claim 13, wherein the C1 esterase inhibitor isolated or purified from human plasma is pasteurized.

16. The pharmaceutical composition of claim 1, wherein the pharmaceutical composition is prepared in liquid form.

17. The pharmaceutical composition of claim 1, wherein the pharmaceutical composition is reconstituted with water from at least one lyophilized powder.

18. The pharmaceutical composition of claim 1, wherein the composition has a viscosity of less than about 20 mPa-s.

19. The pharmaceutical composition of claim 1, wherein the composition has a viscosity of less than about 10 mPa-s.

20. The pharmaceutical composition of claim 1, wherein the C1 esterase inhibitor present in the composition comprises at least 50-60% of the total protein in the composition.

21. The pharmaceutical composition of claim 1, wherein the C1 esterase inhibitor present in the composition comprises at least 75% of the total protein in the composition.

22. The pharmaceutical composition of claim 1, wherein the C1 esterase inhibitor has less than a 10% loss in monomer content when stored for two years at 4° C.

23. The pharmaceutical composition of claim 1, wherein the C1 esterase inhibitor has less than about 20% loss in monomer content loss when stored for one week at 40° C.

24. The pharmaceutical composition of claim 1, wherein the C1 esterase inhibitor has less than about 10% loss in monomer content loss when stored for two weeks at 25° C.

25. The pharmaceutical composition of claim 1, wherein the C1 esterase inhibitor has less than about 2% loss in purity when stored for one week at 40° C.

26. The pharmaceutical composition of claim 1, wherein the C1 esterase inhibitor has less than about 1% loss in purity when stored for one week at 40° C.

27. The pharmaceutical composition of claim 1, wherein the C1 esterase inhibitor has less than about 2% loss in purity when stored for two weeks at 25° C.

28. The pharmaceutical composition of claim 1, wherein the C1 esterase inhibitor has less than about 1% loss in purity when stored for two weeks at 25° C.

29. The pharmaceutical composition of claim 1, wherein the pharmaceutical composition is a monoformulation of active pharmaceutical ingredient, wherein said active pharmaceutical ingredient consists essentially of C1 esterase inhibitor.

* * * * *

SEQUENCE LISTING

<160> NUMBER OF SEQ ID NOS: 1

<210> SEQ ID NO 1
<211> LENGTH: 500
<212> TYPE: PRT

<213> ORGANISM: Homo sapiens

<400> SEQUENCE: 1

```
Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
        35                  40                  45

Val Ile Ser Lys Met Leu Phe Val Glu Pro Ile Leu Glu Val Ser Ser
    50                  55                  60

Leu Pro Thr Thr Asn Ser Thr Thr Asn Ser Ala Thr Lys Ile Thr Ala
65                  70                  75                  80

Asn Thr Thr Asp Glu Pro Thr Thr Gln Pro Thr Thr Glu Pro Thr Thr
                85                  90                  95

Gln Pro Thr Ile Gln Pro Thr Gln Pro Thr Thr Gln Leu Pro Thr Asp
            100                 105                 110

Ser Pro Thr Gln Pro Thr Thr Gly Ser Phe Cys Pro Gly Pro Val Thr
        115                 120                 125

Leu Cys Ser Asp Leu Glu Ser His Ser Thr Glu Ala Val Leu Gly Asp
    130                 135                 140

Ala Leu Val Asp Phe Ser Leu Lys Leu Tyr His Ala Phe Ser Ala Met
145                 150                 155                 160

Lys Lys Val Glu Thr Asn Met Ala Phe Ser Pro Phe Ser Ile Ala Ser
                165                 170                 175

Leu Leu Thr Gln Val Leu Leu Gly Ala Gly Glu Asn Thr Lys Thr Asn
            180                 185                 190

Leu Glu Ser Ile Leu Ser Tyr Pro Lys Asp Phe Thr Cys Val His Gln
        195                 200                 205

Ala Leu Lys Gly Phe Thr Thr Lys Gly Val Thr Ser Val Ser Gln Ile
    210                 215                 220

Phe His Ser Pro Asp Leu Ala Ile Arg Asp Thr Phe Val Asn Ala Ser
225                 230                 235                 240

Arg Thr Leu Tyr Ser Ser Pro Arg Val Leu Ser Asn Asn Ser Asp
                245                 250                 255

Ala Asn Leu Glu Leu Ile Asn Thr Trp Val Ala Lys Asn Thr Asn Asn
            260                 265                 270

Lys Ile Ser Arg Leu Leu Asp Ser Leu Pro Ser Asp Thr Arg Leu Val
        275                 280                 285

Leu Leu Asn Ala Ile Tyr Leu Ser Ala Lys Trp Lys Thr Thr Phe Asp
    290                 295                 300

Pro Lys Lys Thr Arg Met Glu Pro Phe His Phe Lys Asn Ser Val Ile
305                 310                 315                 320

Lys Val Pro Met Met Asn Ser Lys Lys Tyr Pro Val Ala His Phe Ile
                325                 330                 335

Asp Gln Thr Leu Lys Ala Lys Val Gly Gln Leu Gln Leu Ser His Asn
            340                 345                 350

Leu Ser Leu Val Ile Leu Val Pro Gln Asn Leu Lys His Arg Leu Glu
        355                 360                 365

Asp Met Glu Gln Ala Leu Ser Pro Ser Val Phe Lys Ala Ile Met Glu
    370                 375                 380

Lys Leu Glu Met Ser Lys Phe Gln Pro Thr Leu Leu Thr Leu Pro Arg
385                 390                 395                 400
```

-continued

```
Ile Lys Val Thr Thr Ser Gln Asp Met Leu Ser Ile Met Glu Lys Leu
            405                 410                 415

Glu Phe Phe Asp Phe Ser Tyr Asp Leu Asn Leu Cys Gly Leu Thr Glu
            420                 425                 430

Asp Pro Asp Leu Gln Val Ser Ala Met Gln His Gln Thr Val Leu Glu
            435                 440                 445

Leu Thr Glu Thr Gly Val Glu Ala Ala Ala Ser Ala Ile Ser Val
        450                 455                 460

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
                485                 490                 495

Asp Pro Arg Ala
            500
```